United States Patent [19]

Takada et al.

[11] Patent Number: 4,753,951
[45] Date of Patent: Jun. 28, 1988

[54] CONDENSED IMIDAZOPYRIDINE DERIVATIVES USEFUL AS PSYCHOTROPIC AGENTS

[75] Inventors: Susumu Takada, Hyogo; Toshio Fujishita, Osaka; Takashi Sasatani, Nara; Akira Matsushita, Hyogo; Masami Eigyo, Nara, all of Japan

[73] Assignee: Shionogi & Co., Ltd., Osaka, Japan

[21] Appl. No.: 920,162

[22] Filed: Oct. 17, 1986

[30] Foreign Application Priority Data

Oct. 18, 1985 [JP] Japan .............................. 60-234357
May 23, 1986 [JP] Japan .............................. 61-119681

[51] Int. Cl.[4] .................... A61K 31/47; C07D 471/04; C07D 471/14
[52] U.S. Cl. .................................... 514/293; 546/82; 546/83
[58] Field of Search .................... 546/82, 83; 514/293

[56] References Cited

FOREIGN PATENT DOCUMENTS 0145340 6/1985 European Pat. Off. ............. 546/82
238235 8/1986 Fed. Rep. of Germany.

OTHER PUBLICATIONS

Berenyi et al., Chem. Abstracts, vol. 105, 115064c (1986); Abstract of Hung. Teljes HU 34,479, Mar. 28, 1985.
M. M. Abbasi, "Chem. Abstracts", vol. 94, No. 7, Abstract No. 47216f, p. 570, Feb. 16, 1981.

Primary Examiner—Richard A. Schwartz
Assistant Examiner—Bernard I. Dentz
Attorney, Agent, or Firm—Birch, Stewart, Kolasch & Birch

[57] ABSTRACT

A compound of the formula:

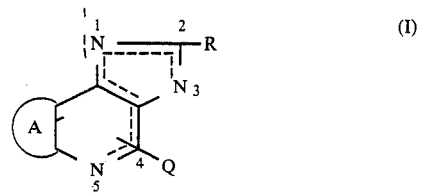

(wherein
R is phenyl optionally substituted by one or two members selected from the group consisting of trifluoromethyl, $C_1$–$C_5$ alkyl, $C_1$–$C_5$ alkoxy, $C_1$–$C_5$ alkylthio, nitro, amino $C_1$–$C_5$ alkanoylamino and $C_1$–$C_5$ alkoxycarbonyl or 5- or 6-membered heterocyclic group optionally substituted by one or two members selected from the group consisting of halogen, $C_1$–$C_5$ alkyl and $C_1$–$C_5$ alkoxy,
Q is hydrogen, $C_1$–$C_5$ alkyl, $C_1$–$C_{10}$ acyl, $C_1$–$C_5$ alkylsulfonyl or $C_6$–$C_{10}$ arylsulfonyl,

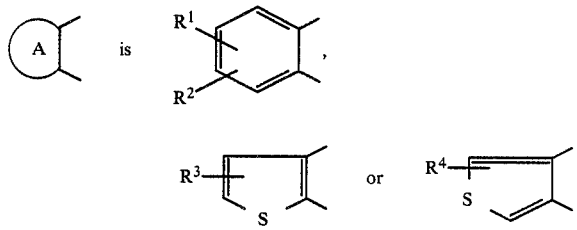

$R^1$, $R^2$, $R^3$, and $R^4$ each is hydrogen, halogen $C_1$–$C_5$ alkyl, $C_1$–$C_5$ alkoxy or $C_1$–$C_5$ haloalkyl,
Q is present on the nitrogen atom of the 1,3 or 5-position, and the dotted line indicates the presence of three double bonds at the position of 2, 3; 3a, 3b; 4, 5 / 1, 3b; 2, 3; 3a, 4 / or 1, 2; 3a, 3b; 4, 5)
or its salt, being useful as psychostimulants or anxiolytics, is provided.

15 Claims, No Drawings

CONDENSED IMIDAZOPYRIDINE DERIVATIVES USEFUL AS PSYCHOTROPIC AGENTS

The present invention relates to condensed imidazopyridine derivatives. More particularly, this invention is directed to condensed imidazopyridine derivatives which have been found to be particularly effective in the treatment of depression or anxiety, to their preparation, to their use and to pharmaceutical formulations containing the compounds.

USSR Pat. No. 509,588 discloses that 1H-2-oxo-3-phenyl-7-methylimidazo[4,5-c]quinoline is useful as a synthetic intermediate to biologically active materials. Abbasi et al, [Monatsh. Chem., 111, 963 (1980)] disclose 3-hydroxy-2-hydroxymethyl-8-methoxy-9-nitro-4-styryl-2H-imidazo[4,5-c]quinoline and its analogs as synthetic intermediates to biologically active materials. Further European Pat. Appln. No. 145,340 describes 2-hydroxyalkyl-1H-imidazo[4,5-c]quinolines useful as bronchodilators or antiviral agents.

The condensed imidazopyridine derivatives of the present invention are those having at 2-position phenyl optionally substituted by one or two members selected from the group consisting of trifluoromethyl, $C_1$-$C_5$ alkyl, $C_1$-$C_5$ alkoxy, $C_1$-$C_5$ alkylthio, nitro, amino, $C_1$-$C_5$ alkanoylamino and $C_1$-$C_5$ alkoxycarbonyl, or 5- or 6-membered heterocyclic group optionally substituted by one or two members selected from the group consisting of halogen, $C_1$-$C_5$ alkyl and $C_1$-$C_5$ alkoxy and are therefore quite different from the compounds disclosed in the above references.

According to the present invention there is provided a condensed imidazopyridine derivative of the formula:

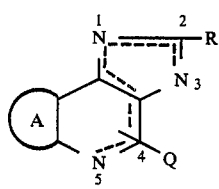
(I)

(wherein

R is phenyl optionally substituted by one or two members selected from the group consisting of trifluoromethyl, $C_1$-$C_5$ alkyl, $C_1$-$C_5$ alkoxy, $C_1$-$C_5$ alkylthio, nitro, amino, $C_1$-$C_5$ alkanoylamino and $C_1$-$C_5$ alkoxycarbonyl, or 5- or 6-membered heterocyclic group optionally substituted by one or two members selected from the group consisting of halogen, $C_1$-$C_5$ alkyl and $C_1$-$C_5$ alkoxy, Q is hydrogen, $C_1$-$C_5$ alkyl, $C_1$-$C_{10}$ acyl, $C_1$-$C_5$ alkylsulfonyl or $C_6$-$C_{10}$ arylsulfonyl,

 is 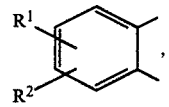,

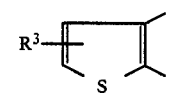 or 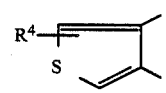

$R^1$, $R^2$, $R^3$ and $R^4$ each is hydrogen, halogen, $C_1$-$C_5$ alkyl, $C_1$-$C_5$ alkoxy or $C_1$-$C_2$ haloalkyl, Q is present on the nitrogen atom of the 1, 3 or 5-position, and the dotted line indicates the presence of three double bonds at the position of 2, 3; 3a, 3b; 4, 5/1, 3b; 2, 3; 3a, 4/or 1, 2; 3a, 3b; 4, 5) or its salt.

The compounds of the present invention have an excellent psychotropic activity such as psychostimulant or anxiolytic activity with no undesirable action to the human beings. Accordingly, the invention also provides a psychotropic formulation comprising as an active ingredient 0.1 to 95% by weight of a compound of the formula (I) associated with at least one carrier, diluent or excipient therefor.

This invention also provides a method of treating a patient suffering from depression or anxiety which comprises administering to the patient a pharmacologically effective amount of a compound of the formula (I).

This invention further provides a process for preparing a compound of the formula (I) which comprises reacting a compound of the formula:

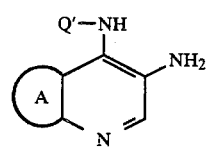
(II)

(wherein Q' is hydrogen or $C_1$-$C_5$ alkyl, and

is as defined above) with an acylating agent to give a compound of the formula:

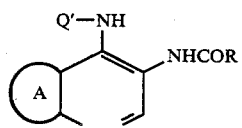
(III)

(wherein

, and Q' each is as defined above) and cyclizing the compound (III) and when Q' is hydrogen, applying the cyclized product to alkylation, acylation or sulfonylation, if necessary.

The term "$C_1$-$C_5$ alkyl" herein employed refers to a straight or branched saturated aliphatic hydrocarbon radical such as methyl, ethyl, propyl, isopropyl, butyl, isobutyl, tert-butyl, pentyl, neopentyl or 1-methylisobutyl.

The term "$C_1$-$C_5$ alkoxy" refers to an alkoxy group containing $C_1$-$C_5$ alkyl moiety and includes methoxy, ethoxy, propoxy, isopropoxy, butoxy and pentyloxy.

The term "$C_1$-$C_5$ alkylthio" refers to an alkylthio group containing $C_1$-$C_5$ alkyl moiety and includes methylthio, ethylthio, propylthio, butylthio isobutylthio and neopentylthio.

The term "$C_1$-$C_5$ alkanoylamino" includes formylamino, acetylamino, propionylamino, butyrylamino, valerylamino and isovalerylamino.

The term "$C_1$-$C_5$ alkoxycarbonyl" includes methoxycarbonyl, ethoxycarbonyl, propoxycarbonyl, butoxycarbonyl and pentyloxycarbonyl.

The term "5- or 6-membered heterocyclic group" includes isoxazolyl, isothiazolyl, pyrazolyl, oxazolyl, thiazolyl, imidazolyl, thiadiazolyl, oxadiazolyl, thienyl, furyl and pyridyl.

The term "$C_1$-$C_{10}$ acyl" includes $C_1$-$C_5$ alkanoyl such as formyl, acetyl, propionyl, butyryl, valeryl or isovaleryl and $C_7$-$C_{11}$ aroyl such as benzoyl, toluoyl or propylbenzoyl.

The term "$C_1$-$C_5$ alkylsulfonyl" includes methylsulfonyl, ethylsulfonyl, propylsulfonyl, isobutylsulfonyl and pentylsulfonyl.

The term "$C_6$-$C_{10}$ arylsulfonyl" includes phenylsulfonyl, tolylsulfonyl, xylylsulfonyl and naphthylsulfonyl.

The term "$C_1$-$C_5$ haloalkyl" includes fluoromethyl, chloroethyl, bromopropyl, iodobutyl and trifluoromethyl.

The term "halogen" includes fluorine, chlorine, bromine and iodine.

The process for preparing the compound (I) is shown by the scheme as follows:

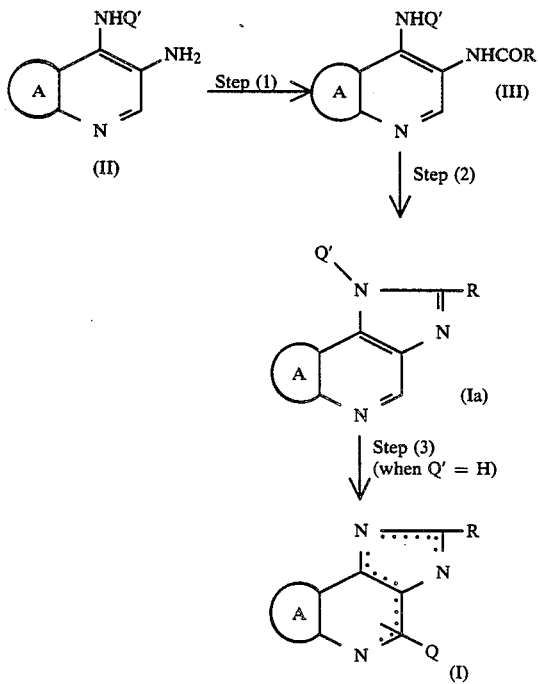

(wherein Q' is hydrogen or $C_1$-$C_5$ alkyl, and

Q and R are as defined above).

Step (1)

The amide (III) can be prepared by reacting the diamine (II) with an acylating reagent. The reaction is performed at a comparatively lower temperarture (e.g. $-10°$ to $5°$ C.) generally in an appropriate solvent, using an acylating agent containing a necessary acyl group.

The solvent includes illustratively dimethylformamide, acetonitrile, chloroform, hexamethylphosphoramide, ether, tetrahydrofuran and mixtures thereof. The acylating reagent refers to an acid halogenide such as acid chloride or acid bromide; a mixed acid anhydride; a mixture of carboxylic acid with thionyl chloride; a mixture of carboxylic acid with a condensing agent such as DCC or polyphosphoric acid.

Step (2)

The compound (Ia) can be prepared by heating the amide (III) in a solvent at a temperature from about $50°$ C. to $250°$ C., preferably $100°$ C. to $250°$ C. in the presence or absence of a cyclizing agent such as polyphosphoric acid, polyphosphoric ester, sulfuric acid, acetic acid or phosphorus pentoxide. The solvent includes illustratively hexamethylphosphoramide, diphenyl ether, glycerin triethyl ether, butyl ether, isoamyl ether, diethylene glycol, triethylene glycol or Dowtherm A (Dow Chemical Co.).

Step (3)

As necessary, the compound (Ia) (Q'=Hydrogen) may be subjected to alkylation, acylation or sulfonylation. The reaction is performed with an alkylating, acylating or sulfonylating agent in an appropriate solvent in the presence of a base such as alkali metal hydride. (e.g. sodium hydride, potassium hydride) or alkali metal alkoxide (e.g. sodium methoxide, potassium ethoxide, sodium isopropoxide) at a temperature of $30°$ to $120°$ C. The alkylating agent includes alkyl halide such as methyl iodide, ethyl bromide, propyl chloride or butyl iodide and dialkyl sulfate such as dimethyl sulfate or diethyl sulfate. The acylating agent includes acyl halide such as acetyl chloride, propionyl bromide, butyryl chloride or benzoyl chloride and acid anhydride such as acetic anhydride or propionic anhydride. The sulfonylating agent includes mesyl chloride, butylsulfonyl chloride and tosyl chloride. As solvents there are exemplified tetrahydrofuran, dioxane, diglyme, dimethylformamide, chloroform and ethanol.

The diamine (II) usable as a starting material can be prepared, as shown below, in accordance with the methods of G. B. Bachman et al., J. Am. Chem. Soc., 69, 365 (1947) and A. R. Surrey et al., J. Am. Chem. Soc., 73, 2413 (1951).

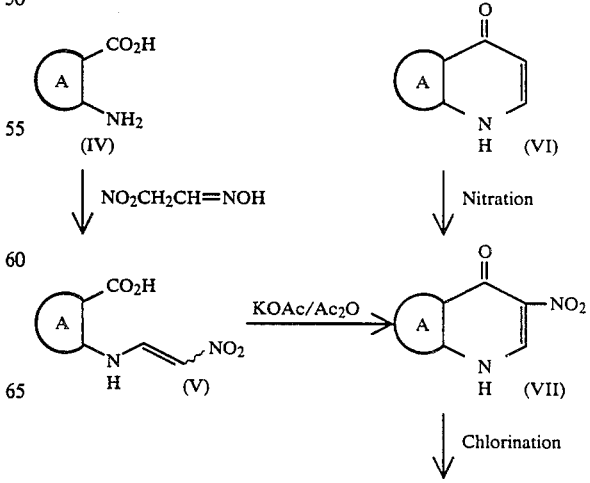

-continued

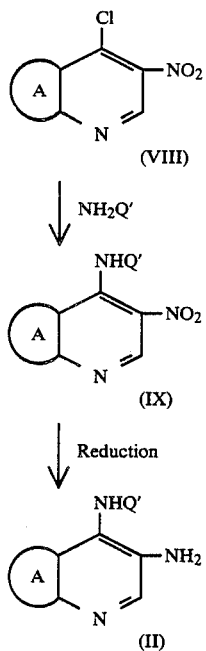

and Q' are as defined above.) The compound (I) includes the following three compounds (Ia, Ib and Ic):

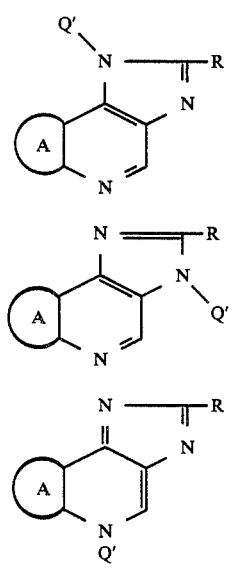

(wherein

Q' and R are as defined above).

The compound (I) can be converted into its pharmaceutically acceptable acid addition salts. Such acids illustratively include an inorganic acid such as hydrochloric acid, sulfuric acid, phosphoric acid or nitric acid and an organic acid such as acetic acid, maleic acid, malic acid, citric acid, lactic acid, succinic acid or methanesulfonic acid.

The compounds (I) or pharmaceutically acceptable acid addition salts thereof have a high affinity to a benzodiazepine receptor, and they are useful as psychotropic agents such as psychostimulants or anxiolytics.

The compounds (I) can be administered orally or parenterally to human beings or other animals. They can be formulated as tablets, capsules, pills, granules, injections, suppositories, and syrups in pharmaceutical practice. As pharmaceutically acceptable carriers, diluents or excipients there are exemplified lactose, sucrose, wheat starch, potato starch, magnesium stearate, gelatin, methyl cellulose, agar, water, and the like. As necessary, appropriate stabilizers, emulsifiers, spreaders, buffers and other pharmaceutical adjuvants can be added. Appropriate daily dosage of the compound (I) is 0.1 to 500 mg in oral route and 0.1 to 300 mg in injection.

The present invention will be explained in more detail by the following Examples, Referential Examples and Formulations.

The abbreviations used in Examples, Referential Examples and Tables have the following meanings.

HMPA: Hexamethylphosphoramide
Me: Methyl
Et: Ethyl
PPA: Polyphosphoric acid
MeCN: Acetonitrile
MeOH: Methanol
EtOH: Ethanol
Et$_2$O: Ether
AcOEt: Ethyl acetate
AcOH: Acetic acid
DMF: Dimethylformamide
(d): Decomposition When Q is hydrogen, the compound (Ia) and (Ib) being a tautomer each other will be named conveniently as said formula (Ia).

For example, 2-(3-trifluoromethylphenyl)-1H-imidazo[4,5-c]quinoline C$_1$ (Example 1) may also be named as 2-(3-trifluoromethylphenyl)-3H-imidazo[4,5-c]quinoline.

EXAMPLE 1

2-(3-Trifluoromethylphenyl)-1H-imidazo[4,5-c]quinoline C$_1$

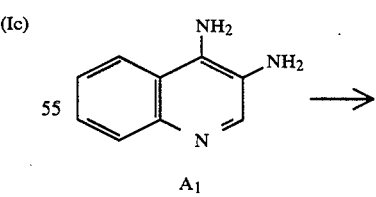

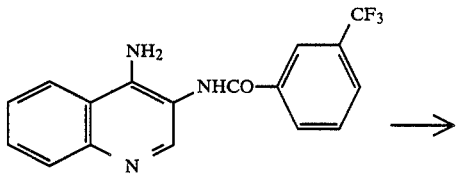

-continued

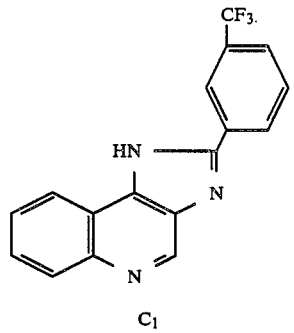

$C_1$

To a solution of 500 mg of 3-trifluoromethylbenzoic acid in 6 ml of anhydrous hexamethylphosphoramide (HMPA) and 0.6 ml of anhydrous acetonitrile is added dropwise 305 mg of thionyl chloride at $-5°$-$0°$ C. under nitrogen. After stirring at the same temperature for 30 minutes, 380 mg of 3,4-diaminoquinoline is added and stirred at $0°$-$5°$ C. for 3 hours. The mixture is diluted with ice-water and neutralized with saturated aqueous sodium bicarbonate. The resulting crystals are filtered, washed with water, and dried to give 780 mg of 4-amino-3-(3-trifluoromethylbenzoylamino)quinoline $B_1$ as a crude product. It is suspended in 15 g of polyphosphoric acid and heated at 120° C. for 4 hours with stirring. The mixture is poured into ice-water and neutralized with 1N sodium hydroxide. The resulting solid is filtered, washed with water and dried. It is chromatographed on silica gel with chloroform-methanol (10:1 v/v) as eluent, yielding 350 mg (47%) of $C_1$ as colorless crystals.

m.p. 254°-256° C. (from ethyl acetate).

Anal. Calcd.(%) (for $C_{17}H_{10}N_3F_3$): C, 65.18; H, 3.22; N, 13.41; F, 18.19. Found (%): C, 64.74; H, 3.54; N, 13.20; F, 18.30.

EXAMPLE 2-3

According to the method illustrated by Example 1, the compounds $C_2$ and $C_3$ are prepared under the conditions shown in Table 1. Table 3 shows the physical properties of these compounds.

TABLE 1

| | | Step (1) | | | |
|---|---|---|---|---|---|
| | | | HMPA—MeCN | | |
| Ex. No. | R | RCO$_2$H (mg) | SOCl$_2$ (mg) | (ml) | (ml) | Compd. A$_1$ (mg) | Reaction Time (hr) |
| 2 | Cl-thiophene- | 420 | 305 | 6 | 0.6 | 380 | 3.5 |
| 3 | F-phenyl- | 370 | 305 | 6 | 0.6 | 380 | 3.5 |

| | | Step (2) | | | Compd. C | | |
|---|---|---|---|---|---|---|---|
| Ex. No. | R | PPA (g) | Temp. (°C.) | Reaction Time (hr) | Yield (mg) | Yield (%) from A$_1$ | Compd. No. |
| 2 | Cl-thiophene- | 15 | 120 | 7.5 | 365 | 54 | $C_2$ |
| 3 | F-phenyl- | 12 | 135 | 4 | 480 | 76 | $C_3$ |

EXAMPLE 4

2-(5-Methylthien-2-yl)-1H-imidazo[4,5-c]quinoline $C_4$

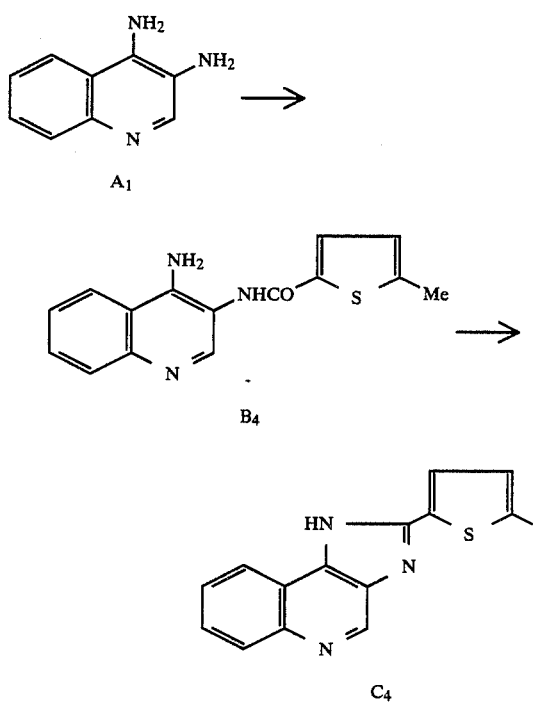

To a solution of 555 mg of 5-methylthiophene-2-carboxylic acid in 9 ml of anhydrous hexamethylphosphoramide and 0.9 ml of anhydrous acetonitrile is added dropwise 455 mg of thionyl chloride at −5°–0° C. under nitrogen. After stirring at the same temperature for 30 minutes, 570 mg of 3,4-diaminoquinoline is added and stirred at 0°–5° C. for 4 hours. The same work-up as described in Example 1 gives 900 mg of 4-amino-3-(5-methylthien-2-ylcarbonylamino)quinoline $B_4$ as a white solid. It is suspended in 15 g of polyphosphate ester and heated at 125° C. with stirring for 3 hours. The mixture is diluted with ice-water and neutralized with 1N sodium hydroxide and extracted with ethyl acetate. The extract is washed with water and saturated sodium chloride, dried over magnesium sulfate, and evaporated. The residue is chromatographed on silica gel with chloroform-methanol (10:1 v/v) as eluent to give 456 mg (48%) of $C_4$ as pale yellow crystals.

m.p. 293°–295° C. (dec.) (from ethanol).

Anal. Calcd. (%) (for $C_{15}H_{11}N_3S$): C, 67.90; H, 4.18; N, 15.84; S, 12.08. Found (%): C, 68.16; H, 4.25; N, 15.76; S, 11.63.

EXAMPLE 5

2-(Pyridin-4-yl)-1H-imidazo[4,5-c]quinoline $C_5$

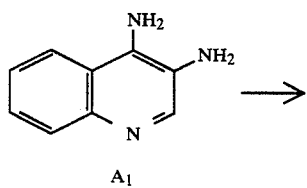

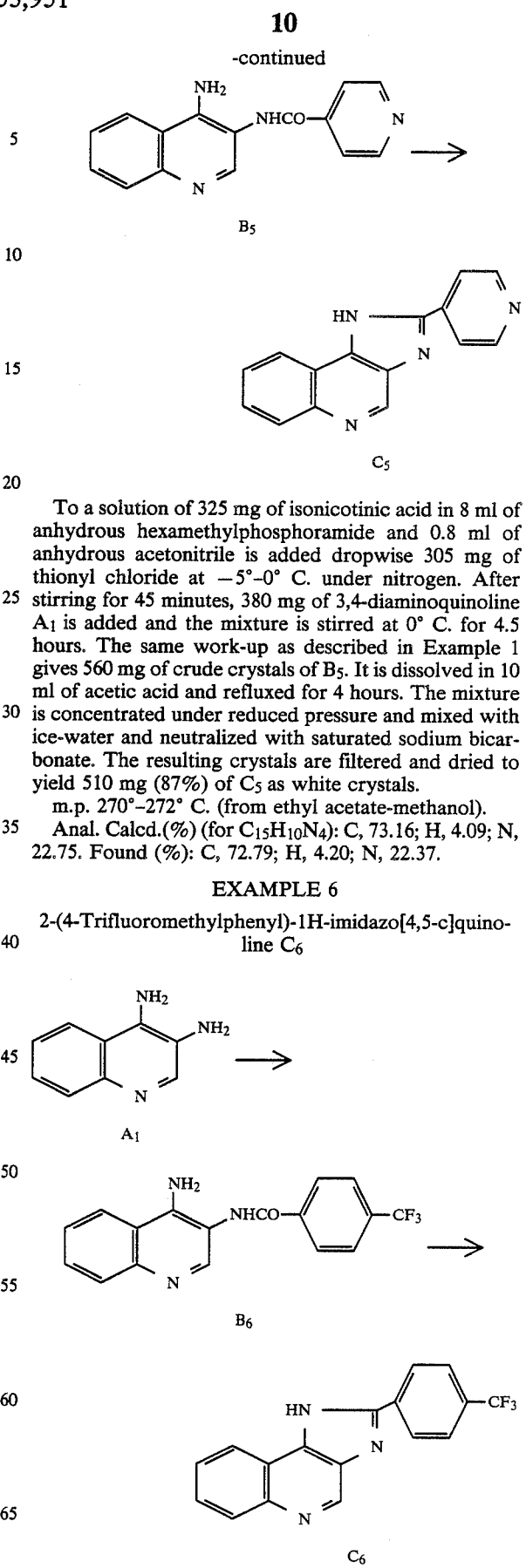

To a solution of 325 mg of isonicotinic acid in 8 ml of anhydrous hexamethylphosphoramide and 0.8 ml of anhydrous acetonitrile is added dropwise 305 mg of thionyl chloride at −5°–0° C. under nitrogen. After stirring for 45 minutes, 380 mg of 3,4-diaminoquinoline $A_1$ is added and the mixture is stirred at 0° C. for 4.5 hours. The same work-up as described in Example 1 gives 560 mg of crude crystals of $B_5$. It is dissolved in 10 ml of acetic acid and refluxed for 4 hours. The mixture is concentrated under reduced pressure and mixed with ice-water and neutralized with saturated sodium bicarbonate. The resulting crystals are filtered and dried to yield 510 mg (87%) of $C_5$ as white crystals.

m.p. 270°–272° C. (from ethyl acetate-methanol).

Anal. Calcd.(%) (for $C_{15}H_{10}N_4$): C, 73.16; H, 4.09; N, 22.75. Found (%): C, 72.79; H, 4.20; N, 22.37.

EXAMPLE 6

2-(4-Trifluoromethylphenyl)-1H-imidazo[4,5-c]quinoline $C_6$

To a solution of 395 mg of 4-trifluoromethylbenzoic acid in 5 ml of anhydrous hexamethylphosphoramide and 0.5 ml of anhydrous acetonitrile is added dropwise 240 mg of thionyl chloride at −5°–0° C. under nitrogen. After stirring at the same temperature for 30 minutes, 300 mg of 3,4-diaminoquinoline $A_1$ is added and stirred at 0°–5° C. for 4 hours. The same work-up as described in Example 1 gives 605 mg of the crude crystals of $B_6$. It is suspended in 10 ml of hexamethylphosphoramide and 2.5 ml of acetic acid, and stirred at 155° C. for 15 minutes under nitrogen. The cooled mixture is diluted with water and neutralized with saturated aqueous sodium bicarbonate. The resulting solid is chromatographed on silica gel with chloroform-methanol (10:1 v/v) as eluent to give 440 mg (75% of $C_6$ as white crystals.

m.p.: >340° C. (from ethanol).

Anal. Calcd. (%) (for $C_{17}H_{10}N_3F_3$): C, 65.18; H, 3.22; N, 13.41; F, 18.19. Found (%): C, 64.95; H, 3.44; N, 13.24; F, 18.10.

EXAMPLE 7–93

According to the method illustrated by Example 6, Compounds $C_7$–$C_{93}$ are prepared under the conditions shown in Table 2. Table 3 shows the physical properties of these compounds.

TABLE 2

$$\underset{A}{\text{[Compound A: 3,4-diamino quinoline]}} \xrightarrow[\text{Step (1)}]{\text{RCO}_2\text{H} \atop \text{SOCl}_2/\text{HMPA}-\text{MeCN}} \underset{B}{\text{[Compound B: 3-NHCOR, 4-NH}_2\text{]}} \xrightarrow[\text{Step (2)}]{\text{HMPA}-\text{AcOH}} \underset{C}{\text{[Compound C: imidazoquinoline]}}$$

| Ex. No. | R | Step (1) | | | | | | | | Step (2) | | | | Compd. C | | Compd. No. |
|---|---|---|---|---|---|---|---|---|---|---|---|---|---|---|---|---|
| | | RCO$_2$H (mg) | SOCl$_2$ (mg) | HMPA (ml) | HMPA–MeCN (ml) | R$^1$ | R$^2$ | Compd. (mg) | Reaction time (hr) | HMPA (ml) | HMPA–AcOH (ml) | Temp. (°C.) | Reaction Time (min) | Yield (mg) | Yield (%) from Compd. A | |
| 7 | 2-thienyl | 670 | 710 | 12 | 1.2 | H | H | 760 | 3.5 | 20 | 5 | 155 | 100 | 875 | 73 | C$_7$ |
| 8 | 2,5-dichloro-thienyl | 520 | 305 | 6 | 0.6 | H | H | 380 | 3.5 | 12 | 3 | 150 | 35 | 560 | 73 | C$_8$ |
| 9 | 5-chloro-thienyl | 420 | 305 | 6 | 0.6 | H | H | 380 | 4.5 | 12 | 3 | 155 | 30 | 390 | 57 | C$_9$ |
| 10 | 2-pyridyl | 325 | 305 | 6 | 0.6 | H | H | 380 | 4.5 | 2 | 4 | 140 | 120 | 315 | 53 | C$_{10}$ |
| 11 | 2-thienyl (methyl) | 335 | 305 | 6 | 0.6 | H | H | 380 | 4.5 | 10 | 2.5 | 150 | 30 | 365 | 61 | C$_{11}$ |
| 12 | 2-furyl | 295 | 305 | 6 | 0.6 | H | H | 380 | 4.5 | 2 | 4 | 140 | 120 | 210 | 37 | C$_{12}$ |
| 13 | 4-MeO-phenyl | 315 | 240 | 5 | 0.5 | H | H | 300 | 4.5 | 8 | 2 | 150 | 30 | 230 | 44 | C$_{13}$ |

TABLE 2-continued

Scheme: Compound A (diaminoquinoline with R¹, R²) →[RCO₂H, SOCl₂/HMPA—MeCN, Step (1)] Compound B (NHCOR, NH₂ quinoline) →[HMPA—AcOH, Step (2)] Compound C (imidazo-fused quinoline with R).

| Ex. No. | R | RCO₂H (mg) | SOCl₂ (mg) | HMPA (ml) | HMPA—MeCN (ml) | R¹ | R² | Compd. (mg) | Reaction time (hr) | HMPA (ml) | HMPA—AcOH (ml) | Temp. (°C.) | Reaction Time (min) | Yield (mg) | Compd. C Yield (%) from Compd. A | Compd. No. |
|---|---|---|---|---|---|---|---|---|---|---|---|---|---|---|---|---|
| 14 | phenyl | 320 | 305 | 6 | 0.6 | H | H | 380 | 3.5 | 10 | 2.5 | 145 | 15 | 430 | 13 | C₁₄ |
| 15 | 5-chlorothiophen-2-yl | 280 | 200 | 5 | 0.5 | 6-Cl | H | 300 | 4.5 | 8 | 2 | 150 | 60 | 270 | 54 | C₁₅ |
| 16 | 4-fluorophenyl | 240 | 200 | 5 | 0.5 | 6-Cl | H | 300 | 4.5 | 8 | 2 | 155 | 30 | 275 | 60 | C₁₆ |
| 17 | furan-3-yl | 295 | 305 | 6 | 0.6 | H | H | 380 | 4.5 | 10 | 2.5 | 150 | 30 | 320 | 60 | C₁₇ |
| 18 | 4-(methylthio)phenyl | 350 | 240 | 5 | 0.5 | H | H | 300 | 4.5 | 8 | 2 | 150 | 30 | 340 | 62 | C₁₈ |
| 19 | 4-(acetamido)phenyl | 370 | 240 | 5 | 0.5 | H | H | 300 | 4.5 | 10 | 2.5 | 150 | 15 | 375 | 66 | C₁₉ |

TABLE 2-continued

Reaction scheme:

Compound A (with NH$_2$ groups at positions 3,4 on quinoline): R$^1$, R$^2$ substituents
→ Step (1): RCO$_2$H, SOCl$_2$/HMPA—MeCN → Compound B (H$_2$N, NHCOR)
→ Step (2): HMPA—AcOH → Compound C (HN-R, N$_3$ fused ring)

| Ex. No. | R | Step (1) RCO$_2$H (mg) | SOCl$_2$ (mg) | HMPA (ml) | HMPA—MeCN (ml) | R$^1$ | R$^2$ | Compd. (mg) | Reaction time (hr) | Step (2) HMPA (ml) | HMPA—AcOH (ml) | Temp. (°C.) | Reaction Time (min) | Yield (mg) | Yield (%) from Compd. A | Compd. C No. |
|---|---|---|---|---|---|---|---|---|---|---|---|---|---|---|---|---|
| 20 | 3-F-C$_6$H$_4$ | 290 | 240 | 5 | 0.5 | H | H | 300 | 4.5 | 8 | 2 | 165 | 15 | 330 | 67 | C$_{20}$ |
| 21 | 2-F-C$_6$H$_4$ | 290 | 240 | 5 | 0.5 | H | H | 300 | 4.5 | 4 | 4 | 150 | 90 | 350 | 71 | C$_{21}$ |
| 22 | 2-Cl-C$_6$H$_4$ | 325 | 240 | 5 | 0.5 | H | H | 300 | 4.5 | 8 | 2 | 155 | 45 | 310 | 59 | C$_{22}$ |
| 23 | 2-methyl-5-chlorothien-3-yl | 330 | 240 | 5 | 0.5 | H | H | 300 | 4.5 | 8 | 2 | 165 | 30 | 380 | 71 | C$_{23}$ |
| 24 | 3-MeO-C$_6$H$_4$ | 315 | 240 | 5 | 0.5 | H | H | 300 | 4.5 | 12 | 4 | 165 | 60 | 370 | 71 | C$_{24}$ |

TABLE 2-continued
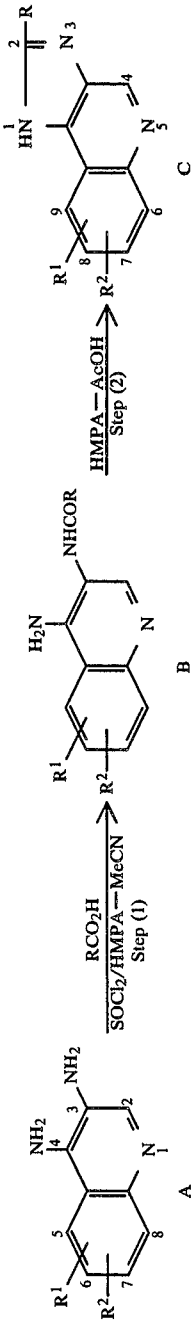
| Ex. No. | R | Step (1) RCO₂H (mg) | SOCl₂ (mg) | HMPA (ml) | HMPA—MeCN (ml) | R¹ | R² | Compd. B (mg) | Reaction time (hr) | Step (2) HMPA (ml) | HMPA—AcOH (ml) | Temp. (°C.) | Reaction Time (min) | Yield (mg) | Compd. C Yield (%) from Compd. A | Compd. No. |
|---|---|---|---|---|---|---|---|---|---|---|---|---|---|---|---|---|
| 25 | Me-thiophene | 380 | 305 | 6 | 0.6 | H | H | 380 | 4.5 | 10 | 2.5 | 155 | 10 | 350 | 55 | C₂₅ |
| 26 | MeO₂C-phenyl | 375 | 240 | 5 | 0.5 | H | H | 300 | 4.5 | 12 | 3 | 155 | 30 | 255 | 45 | C₂₆ |
| 27 | 2,4-F₂-phenyl | 425 | 305 | 6 | 0.5 | H | H | 380 | 4.5 | 8 | 2 | 155 | 10 | 520 | 77 | C₂₇ |
| 28 | 3,4-(MeO)₂-phenyl | 380 | 240 | 5 | 0.5 | H | H | 300 | 3.5 | 8 | 2 | 165 | 30 | 280 | 49 | C₂₈ |
| 29 | 3,5-(MeO)₂-phenyl | 380 | 240 | 5 | 0.5 | H | H | 300 | 3.5 | 8 | 2 | 165 | 20 | 390 | 68 | C₂₉ |

TABLE 2-continued

Step (1): A + RCO₂H, SOCl₂/HMPA—MeCN → B (NHCOR intermediate)
Step (2): B, HMPA—AcOH → C

| Ex. No. | R | Step (1) | | | | | | | Step (2) | | | | Compd. C | |
|---|---|---|---|---|---|---|---|---|---|---|---|---|---|---|
| | | RCO₂H (mg) | SOCl₂ (mg) | HMPA (ml) | HMPA—MeCN (ml) | R¹ | R² | Compd. (mg) | Reaction time (hr) | HMPA (ml) | HMPA—AcOH (ml) | Temp. (°C.) | Reaction Time (min) | Yield (mg) | Yield (%) from Compd. A | Compd. No. |
| 30 | 4-O₂N-C₆H₄ | 350 | 240 | 5 | 0.5 | H | H | 300 | 5.5 | 10 | 2.5 | 165 | 60 | 460 | 84 | C₃₀ |
| 31 | 2,3-F₂-C₆H₃ | 330 | 240 | 5 | 0.5 | H | H | 300 | 4.5 | 4 | 4 | 145 | 45 | 480 | 91 | C₃₁ |
| 32 | 2,5-F₂-C₆H₃ | 330 | 240 | 5 | 0.5 | H | H | 300 | 4.5 | 4 | 4 | 140 | 30 | 470 | 89 | C₃₂ |
| 33 | 3,4-F₂-C₆H₃ | 330 | 240 | 5 | 0.5 | H | H | 300 | 3.5 | 6 | 4 | 155 | 30 | 430 | 81 | C₃₃ |
| 34 | 2-Cl-3-Me-5-Me-thiophene | 465 | 305 | 6 | 0.6 | | | 380 | 4.5 | 10 | 0 | 225 | 30 | 565 | 79 | C₃₄ |

TABLE 2-continued

A: structure with NH2, NH2 on pyridine fused to benzene ring bearing R1, R2
→ RCO2H, SOCl2/HMPA–MeCN, Step (1) →
B: structure with H2N, NHCOR
→ HMPA–AcOH, Step (2) →
C: structure with HN–C(=O)–R, N3

| Ex. No. | R | Step (1) | | | | | | | | Step (2) | | | | Compd. C | |
|---|---|---|---|---|---|---|---|---|---|---|---|---|---|---|---|
| | | RCO2H (mg) | SOCl2 (mg) | HMPA (ml) | HMPA–MeCN (ml) | R1 | R2 | Compd. (mg) | Reaction time (hr) | HMPA (ml) | HMPA–AcOH (ml) | Temp. (°C) | Reaction Time (min) | Yield (mg) | Yield (%) from Compd. A | Compd. No. |
| 35 | 2-thienyl | 265 | 240 | 5 | 0.5 | 7-Cl | H | 365 | 4.5 | 8 | 2 | 160 | 30 | 380 | 71 | C35 |
| 36 | 4-F-phenyl | 290 | 240 | 5 | 0.5 | 7-Cl | H | 365 | 4.5 | 8 | 2 | 160 | 15 | 385 | 69 | C36 |
| 37 | 5-Me-2-thienyl | 375 | 305 | 6 | 0.5 | H | H | 380 | 4.5 | 10 | 2.5 | 160 | 45 | 540 | 85 | C37 |
| 38 | 5-Me-2-thienyl | 295 | 240 | 5 | 0.5 | 7-Cl | H | 365 | 4.5 | 8 | 2 | 165 | 40 | 400 | 71 | C38 |
| 39 | 5-Me-2-thienyl | 295 | 240 | 5 | 0.5 | 7-Cl | H | 365 | 4.5 | 8 | 2 | 170 | 10 | 380 | 67 | C39 |
| 40 | 4-F-phenyl | 290 | 240 | 5 | | 6-F | H | 330 | 4.5 | 8 | 2 | 165 | 10 | 425 | 81 | C40 |

TABLE 2-continued $$\underset{A}{\overset{NH_2}{\underset{R^1}{\bigvee}}\overset{3}{\underset{N}{\bigvee}}\overset{NH_2}{\underset{8}{\bigvee}}} \xrightarrow[\text{Step (1)}]{\text{RCO}_2\text{H}} \underset{B}{\overset{H_2N}{\underset{R^1}{\bigvee}}\overset{NHCOR}{\underset{N}{\bigvee}}} \xrightarrow[\text{Step (2)}]{\text{HMPA—AcOH}} \underset{C}{\overset{HN}{\underset{R^1}{\bigvee}}\overset{1}{\underset{N}{\bigvee}}\overset{2}{\underset{R^2}{\bigvee}}R}$$

| Ex. No. | R | Step (1) | | | | | | | | Step (2) | | | | Compd. C | |
|---|---|---|---|---|---|---|---|---|---|---|---|---|---|---|---|
| | | RCO$_2$H (mg) | SOCl$_2$ (mg) | HMPA (ml) | MeCN (ml) | R$^1$ | R$^2$ | Compd. (mg) | Reaction time (hr) | HMPA (ml) | AcOH (ml) | Temp. (°C.) | Reaction Time (min) | Yield (mg) | Yield (%) from Compd. A | Compd. No. |
| 41 | Me–[thiophene]– | 295 | 240 | 5 | 0.5 | 6-F | H | 330 | 4.5 | 8 | 2 | 160 | 15 | 390 | 74 | C$_{41}$ |
| 42 | [thiophene] | 206 | 181 | 4 | 0.4 | 7-Me | H | 250 | 4 | 5.7 | 1.4 | 180 | 30 | 323 | 83 | C$_{42}$ |
| 43 | Me–[thiophene]– | 228 | 181 | 4 | 0.4 | 7-Me | H | 250 | 5 | 6 | 1.5 | 180 | 60 | 325 | 81 | C$_{43}$ |
| 44 | [thiophene] | 214 | 192 | 5 | 0.5 | 6-Cl | 7-Cl | 343 | 2.5 | 8 | 2 | 170 | 40 | 314 | 65 | C$_{44}$ |
| 45 | Me–[isoxazole]– | 1770 | 1250 | 20 | 2 | H | H | 2000 | 3 | 36 | 9 | 180 | 40 | 2940 | 93.6 | C$_{45}$ |
| 46 | Et–[isoxazole]– | 274 | 220 | 4 | 0.4 | H | H | 280 | 4 | 6 | 1.5 | 180 | 30 | 338 | 73 | C$_{46}$ |
| 47 | Et–[isoxazole]– | 245 | 198 | 4 | 0.4 | 7-F | H | 280 | 4 | 5 | 1.2 | 180 | 35 | 309 | 71 | C$_{47}$ |

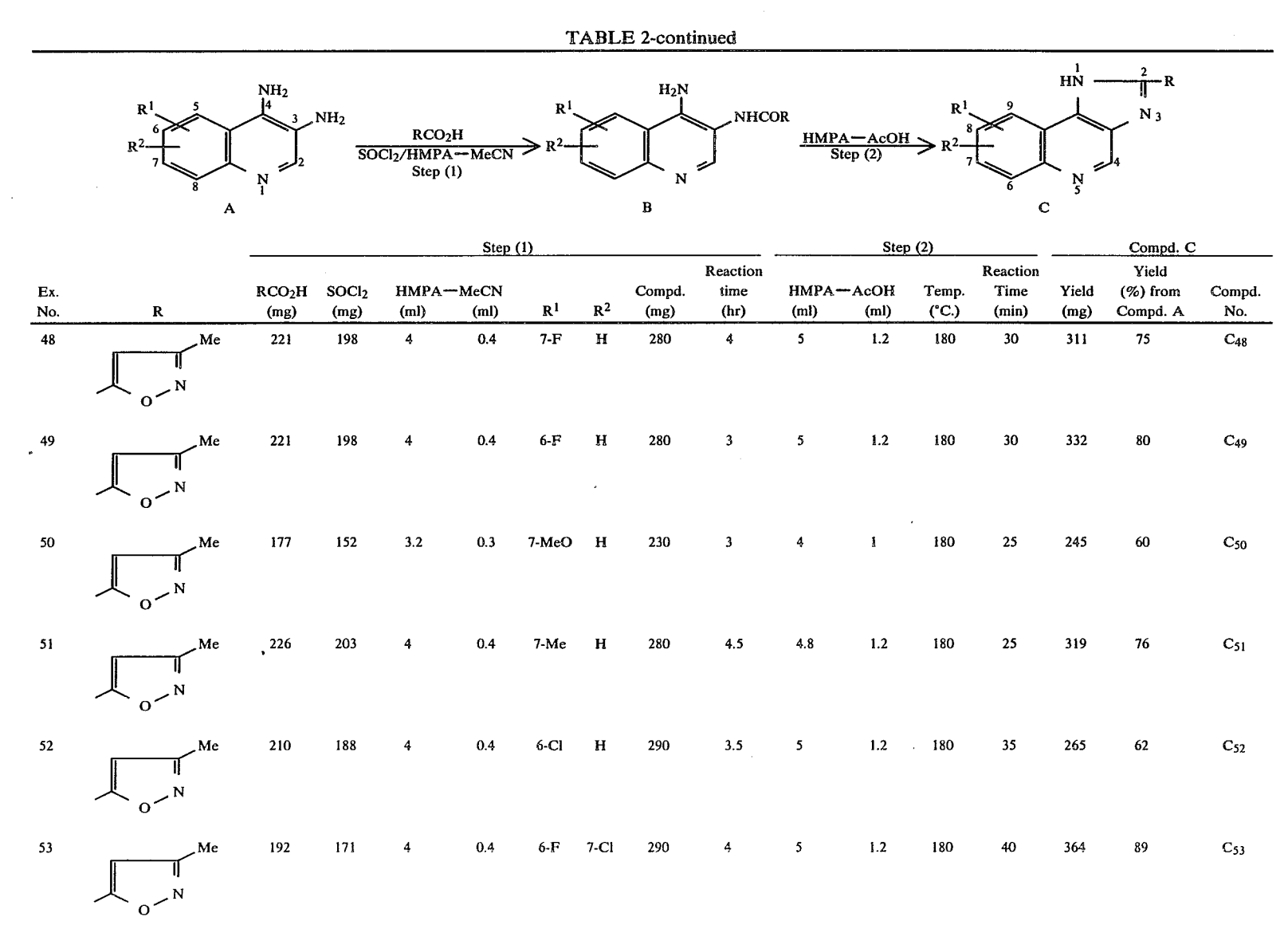

TABLE 2-continued

Step (1): A + RCO₂H →(SOCl₂/HMPA—MeCN) B

Step (2): B →(HMPA—AcOH) C where A has NH₂ groups at 3,4 positions of quinoline (with R¹, R² substituents), B has NH₂ and NHCOR, and C is the cyclized product with R group.

| Ex. No. | R | Step (1) | | | | | | | Step (2) | | | | Compd. C | |
|---|---|---|---|---|---|---|---|---|---|---|---|---|---|---|
| | | RCO₂H (mg) | SOCl₂ (mg) | HMPA (ml) | MeCN (ml) | R¹ | R² | Compd. (mg) | Reaction time (hr) | HMPA (ml) | AcOH (ml) | Temp. (°C) | Reaction Time (min) | Yield (mg) | Yield (%) from Compd. A | Compd. No. |
| 48 | Me-C(=N-O-)CH=C(Me) | 221 | 198 | 4 | 0.4 | 7-F | H | 280 | 4 | 5 | 1.2 | 180 | 30 | 311 | 75 | C₄₈ |
| 49 | Me-C(=N-O-)CH=C(Me) | 221 | 198 | 4 | 0.4 | 6-F | H | 280 | 3 | 5 | 1.2 | 180 | 30 | 332 | 80 | C₄₉ |
| 50 | Me-C(=N-O-)CH=C(Me) | 177 | 152 | 3.2 | 0.3 | 7-MeO | H | 230 | 3 | 4 | 1 | 180 | 25 | 245 | 60 | C₅₀ |
| 51 | Me-C(=N-O-)CH=C(Me) | 226 | 203 | 4 | 0.4 | 7-Me | H | 280 | 4.5 | 4.8 | 1.2 | 180 | 25 | 319 | 76 | C₅₁ |
| 52 | Me-C(=N-O-)CH=C(Me) | 210 | 188 | 4 | 0.4 | 6-Cl | H | 290 | 3.5 | 5 | 1.2 | 180 | 35 | 265 | 62 | C₅₂ |
| 53 | Me-C(=N-O-)CH=C(Me) | 192 | 171 | 4 | 0.4 | 6-F | 7-Cl | 290 | 4 | 5 | 1.2 | 180 | 40 | 364 | 89 | C₅₃ |

TABLE 2-continued
| | | Step (1) | | | | | | Reaction time (hr) | | Step (2) | | | | | Compd. C | |
|---|---|---|---|---|---|---|---|---|---|---|---|---|---|---|---|---|
| Ex. No. | R | RCO₂H (mg) | SOCl₂ (mg) | HMPA (ml) | HMPA—MeCN (ml) | R¹ | R² | | Compd. (mg) | HMPA (ml) | HMPA—AcOH (ml) | Temp. (°C) | Reaction Time (min) | Yield (mg) | Yield (%) from Compd. A | Compd. No. |
| 54 | Me-isoxazole | 210 | 188 | 4 | 0.4 | 7-Cl | H | | 290 | 4.8 | 1.2 | 180 | 30 | 281 | 67 | C₅₄ |
| 55 | Me-isoxazole | 184 | 166 | 4 | 0.4 | 7-CF₃ | H | | 300 | 5 | 1.2 | 180 | 35 | 343 | 83 | C₅₅ |
| 56 | Me-isoxazole | 216 | 214 | 5 | 0.5 | 5-Cl | 7-Cl | | 290 | 8 | 2 | 160 | 40 | 316 | 66 | C₅₆ |
| 57 | Me-isoxazole | 229 | 205 | 4 | 0.4 | 8-F | H | | 290 | 4 | 1 | 180 | 30 | 334 | 77 | C₅₇ |
| 58 | methylisoxazole | 249 | 250 | 4 | 0.4 | H | H | | 318 | 6 | 1.5 | 180 | 20 | 382 | 82 | C₅₈ |
| 59 | methylisoxazole | 193 | 194 | 4 | 0.4 | 7-Cl | H | | 300 | 4 | 1 | 180 | 15 | 307 | 75 | C₅₉ |
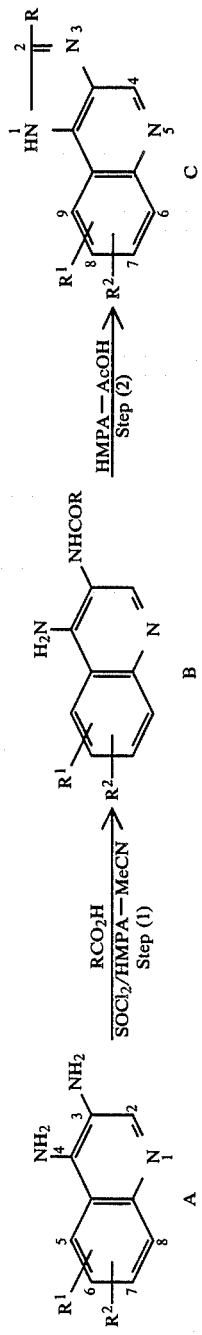
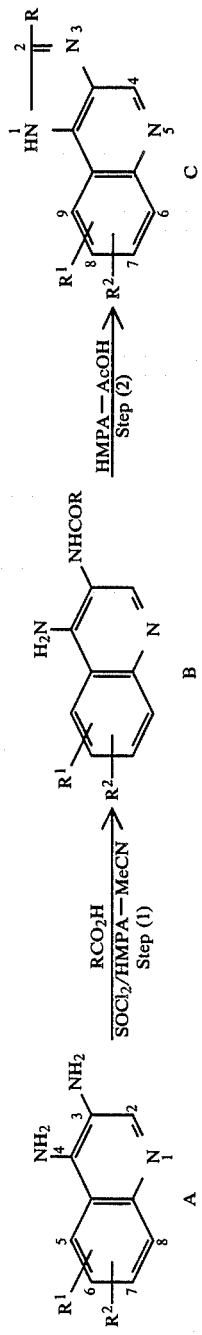
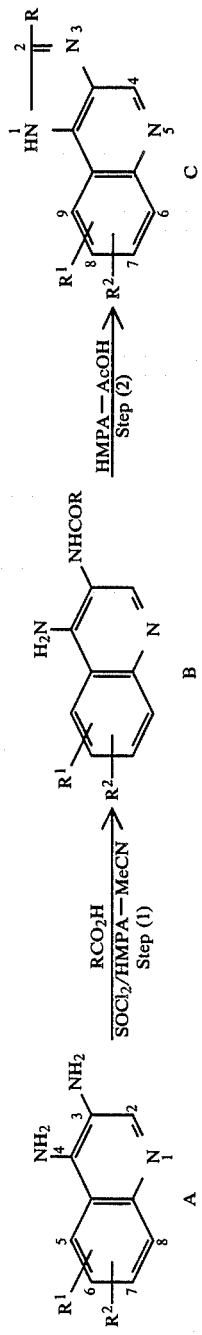

TABLE 2-continued
| | | Step (1) RCO$_2$H SOCl$_2$/HMPA—MeCN | | | | | | | | Step (2) HMPA—AcOH | | | | | Compd. C | |
|---|---|---|---|---|---|---|---|---|---|---|---|---|---|---|---|---|
| Ex. No. | R | RCO$_2$H (mg) | SOCl$_2$ (mg) | HMPA (ml) | HMPA—MeCN (ml) | R$^1$ | R$^2$ | Compd. (mg) | Reaction time (hr) | HMPA (ml) | HMPA—AcOH (ml) | Temp. (°C) | Reaction Time (min) | Yield (mg) | Yield (%) from Compd. A | Compd. No. |
| 60 | 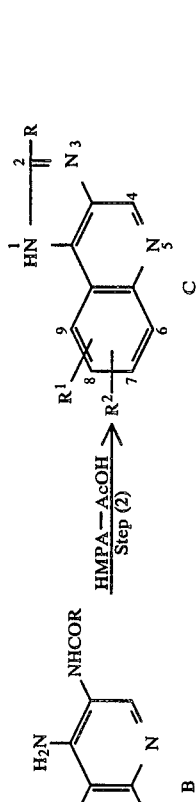 | 210 | 211 | 4 | 0.4 | 7-F | H | 300 | 3 | 4 | 1 | 180 | 20 | 321 | 76 | C$_{60}$ |
| 61 | 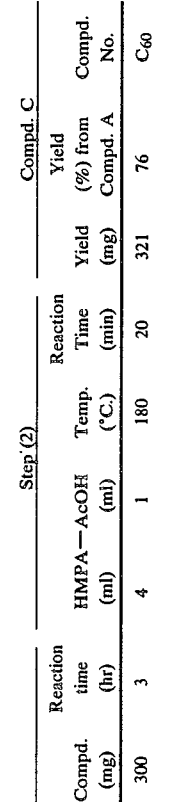 | 280 | 250 | 4.6 | 0.5 | H | H | 318 | 3.5 | 5.6 | 1.4 | 180 | 15 | 326 | 70 | C$_{61}$ |
| 62 | 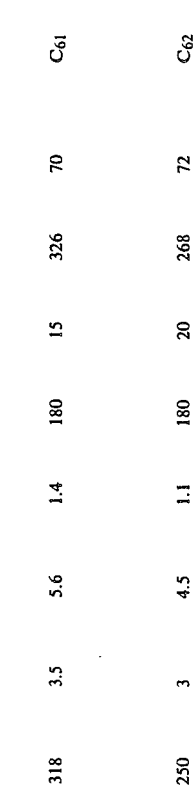 | 198 | 177 | 4 | 0.4 | 7-F | H | 250 | 3 | 4.5 | 1.1 | 180 | 20 | 268 | 72 | C$_{62}$ |
| 63 | 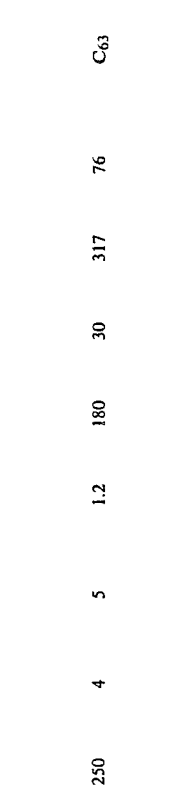 | 244 | 197 | 4 | 0.4 | H | H | 250 | 4 | 5 | 1.2 | 180 | 30 | 317 | 76 | C$_{63}$ |
| 64 | 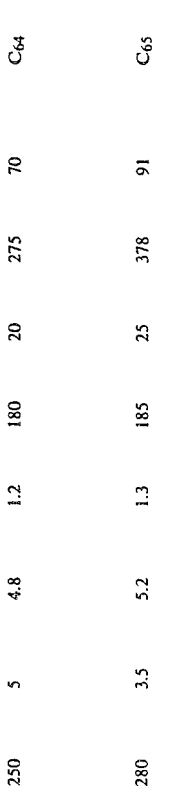 | 220 | 177 | 4 | 0.4 | 7-F | H | 250 | 5 | 4.8 | 1.2 | 180 | 20 | 275 | 70 | C$_{64}$ |
| 65 |  | 221 | 198 | 4 | 0.4 | 6-F | H | 280 | 3.5 | 5.2 | 1.3 | 185 | 25 | 378 | 91 | C$_{65}$ |

TABLE 2-continued $$A \xrightarrow[\text{Step (1)}]{\text{RCO}_2\text{H} \atop \text{SOCl}_2/\text{HMPA}-\text{MeCN}} B \xrightarrow[\text{Step (2)}]{\text{HMPA}-\text{AcOH}} C$$

Compound A: 3,4-diamino quinoline with $R^1$, $R^2$ substituents
Compound B: 4-amino-3-NHCOR quinoline
Compound C: imidazo-fused quinoline with $R^1$, $R^2$ substituents

| Ex. No. | R | Step (1) RCO₂H (mg) | SOCl₂ (mg) | HMPA (ml) | HMPA—MeCN (ml) | R¹ | R² | Compd. (mg) | Reaction time (hr) | Step (2) HMPA (ml) | HMPA—AcOH (ml) | Temp. (°C.) | Reaction Time (min) | Yield (mg) | Compd. C Yield (%) from Compd. A | Compd. No. |
|---|---|---|---|---|---|---|---|---|---|---|---|---|---|---|---|---|
| 66 | Me-isoxazolyl (O–N) | 203 | 182 | 4 | 0.4 | 7-Cl | H | 280 | 5 | 4.8 | 1.2 | 185 | 20 | 291 | 72 | C₆₆ |
| 67 | Me-isothiazolyl (S–N) | 229 | 181 | 4 | 0.4 | H | H | 230 | 3.5 | 5 | 1.2 | 180 | 15 | 303 | 81 | C₆₇ |
| 68 | Me-thiazolyl | 229 | 181 | 4 | 0.4 | H | H | 230 | 3.5 | 5 | 1.2 | 180 | 25 | 318 | 83 | C₆₈ |
| 69 | Me-oxadiazolyl | 223 | 197 | 4 | 0.4 | H | H | 250 | 4 | 4.4 | 1.1 | 180 | 40 | 244 | 61 | C₆₉ |
| 70 | Me-thiadiazolyl | 225 | 197 | 4 | 0.4 | H | H | 250 | 4.5 | 4.8 | 1.2 | 180 | 35 | 298 | 77 | C₇₀ |
| 71 | Me-thiazolyl | 336 | 268 | 4 | 0.4 | H | H | 340 | 5 | 5 | 1.2 | 180 | 30 | 457 | 82 | C₇₁ |

TABLE 2-continued

| Ex. No. | R | Step (1) RCO₂H SOCl₂/HMPA—MeCN | | | | | | | | Step (2) HMPA—AcOH | | | | | Compd. C | |
|---|---|---|---|---|---|---|---|---|---|---|---|---|---|---|---|---|
| | | RCO₂H (mg) | SOCl₂ (mg) | HMPA (ml) | HMPA—MeCN (ml) | R¹ | R² | Compd. (mg) | Reaction time (hr) | HMPA (ml) | HMPA—AcOH (ml) | Temp. (°C.) | Reaction Time (min) | Yield (mg) | Yield (%) from Compd. A | Compd. No. |
| 72 | (4-methyl-2-thiazolyl) | 298 | 238 | 4 | 0.4 | H | H | 300 | 4 | 4 | 1 | 180 | 25 | 318 | 65 | C₇₂ |
| 73 | (2-methyl-4-thiazolyl) | 303 | 268 | 4 | 0.4 | H | H | 340 | 6 | 4 | 1 | 180 | 30 | 339 | 65 | C₇₃ |
| 74 | (4-methyl-5-thiazolyl) | 303 | 268 | 4 | 0.4 | H | H | 340 | 4 | 4 | 1 | 180 | 40 | 360 | 67 | C₇₄ |
| 75 | (1,3-dimethyl-pyrazol-5-yl) | 330 | 305 | 6 | 0.6 | H | H | 380 | 4.5 | 14 | 3.5 | 175 | 60 | 310 | 52 | C₇₅ |
| 76 | (1,5-dimethyl-pyrazol-3-yl) | 330 | 305 | 6 | 0.6 | H | H | 380 | 4.5 | 6 | 1 | 150 | 30 | 430 | 72 | C₇₆ |
| 77 | (2-methyl-5-oxazolyl) | 670 | 610 | 10 | 1 | H | H | 760 | 4.5 | 12 | 3 | 160 | 30 | 850 | 71 | C₇₇ |

TABLE 2-continued $$\underset{A}{\overset{NH_2}{\underset{R^1}{\bigotimes}}\overset{NH_2}{\underset{8}{\bigotimes}}} \xrightarrow[\text{Step (1)}]{RCO_2H \atop SOCl_2/HMPA-MeCN} \underset{B}{\overset{H_2N}{\underset{R^1}{\bigotimes}}\overset{NHCOR}{\underset{N}{\bigotimes}}} \xrightarrow[\text{Step (2)}]{HMPA-AcOH} \underset{C}{\overset{HN\overset{1}{\frown}\overset{R}{\underset{N_3}{\bigotimes}}}{\underset{R^1}{\bigotimes}\overset{8}{\underset{7}{\bigotimes}}\overset{9}{\underset{R^2}{\bigotimes}}\overset{4}{\underset{N_5}{\bigotimes}}}}$$

| Ex. No. | R | Step (1) | | | | | | | | Step (2) | | | | Compd. C | | |
|---|---|---|---|---|---|---|---|---|---|---|---|---|---|---|---|---|
| | | RCO₂H (mg) | SOCl₂ (mg) | HMPA (ml) | HMPA—MeCN (ml) | R¹ | R² | Compd. (mg) | Reaction time (hr) | HMPA (ml) | HMPA—AcOH (ml) | Temp. (°C.) | Reaction Time (min) | Yield (mg) | Yield (%) from Compd. A | Compd. No. |
| 78 | (thiazole-Me) | 303 | 268 | 4 | 0.4 | H | H | 340 | 4 | 4 | 1 | 180 | 40 | 360 | 67 | C₇₈ |
| 79 | (isoxazole-Me) | 193 | 194 | 4 | 0.4 | 8-Cl | H | 300 | 3 | 4 | 1 | 180 | 20 | 293 | 72 | C₇₉ |
| 80 | (isoxazole-Me) | 246 | 248 | 4 | 0.4 | 8-F | H | 350 | 3 | 4 | 1 | 180 | 25 | 303 | 60 | C₈₀ |
| 81 | (isoxazole-Me) | 562 | 565 | 7 | 0.7 | 6-F | H | 800 | 5 | 8 | 2 | 180 | 25 | 862 | 75.4 | C₈₁ |
| 82 | (isoxazole-Me) | 244 | 245 | 4 | 0.4 | 6-OMe | H | 370 | 4 | 5 | 1.2 | 180 | 30 | 403 | 77.4 | C₈₂ |
| 83 | (isoxazole-Me) | 497 | 500 | 7 | 0.7 | 7-F | H | 708 | 5 | 0 | 9 | 118 | 60 | 679 | 808 | C₈₃ |
| 84 | (isoxazole-Me) | 249 | 250 | 4 | 0.4 | 8-F | H | 354 | 4 | 4.8 | 1.2 | 180 | 30 | 395 | 77.8 | C₈₄ |

TABLE 2-continued
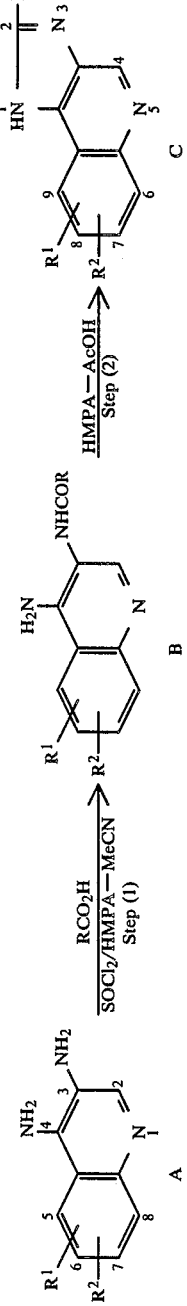
| Ex. No. | R | Step (1) RCO₂H (mg) | SOCl₂ (mg) | HMPA (ml) | HMPA—MeCN (ml) | R¹ | R² | Compd. B (mg) | Reaction time (hr) | HMPA (ml) | HMPA—AcOH (ml) | Step (2) Temp. (°C.) | Reaction Time (min) | Yield (mg) | Compd. C Yield (%) from Compd. A | Compd. No. |
|---|---|---|---|---|---|---|---|---|---|---|---|---|---|---|---|---|
| 85 | 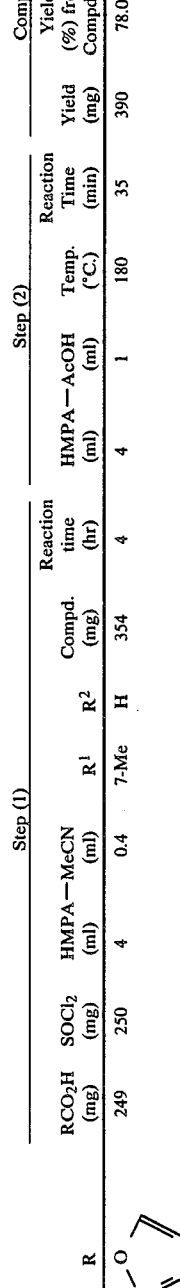 | 249 | 250 | 4 | 0.4 | 7-Me | H | 354 | 4 | 4 | 1 | 180 | 35 | 390 | 78.0 | C₈₅ |
| 86 | 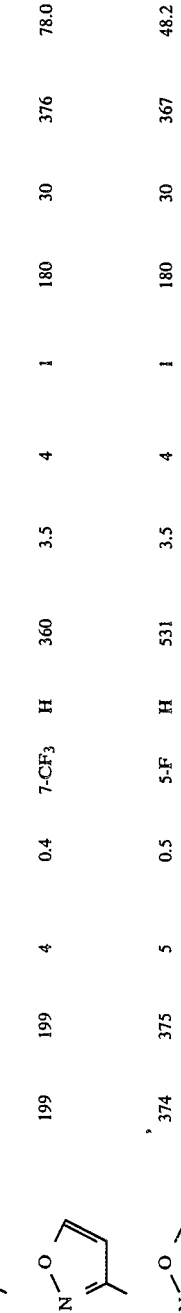 | 199 | 199 | 4 | 0.4 | 7-CF₃ | H | 360 | 3.5 | 4 | 1 | 180 | 30 | 376 | 78.0 | C₈₆ |
| 87 | 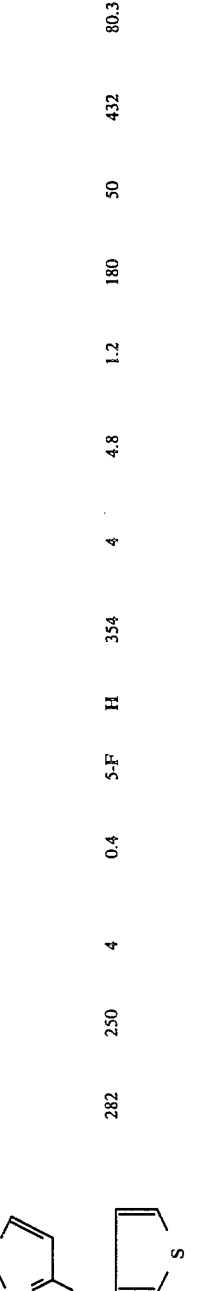 | 374 | 375 | 5 | 0.5 | 5-F | H | 531 | 3.5 | 4 | 1 | 180 | 30 | 367 | 48.2 | C₈₇ |
| 88 | 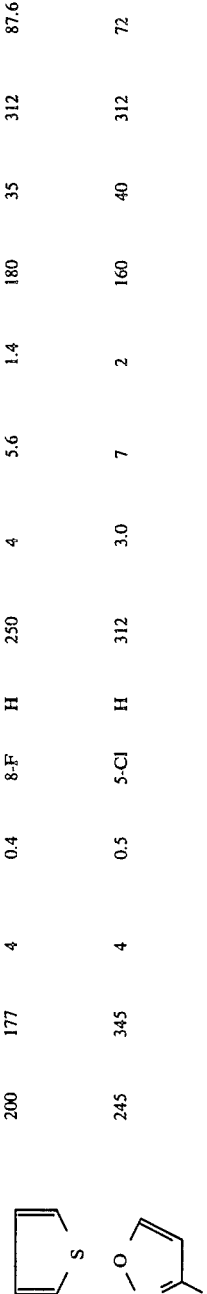 | 282 | 250 | 4 | 0.4 | 5-F | H | 354 | 4 | 4.8 | 1.2 | 180 | 50 | 432 | 80.3 | C₈₈ |
| 89 | 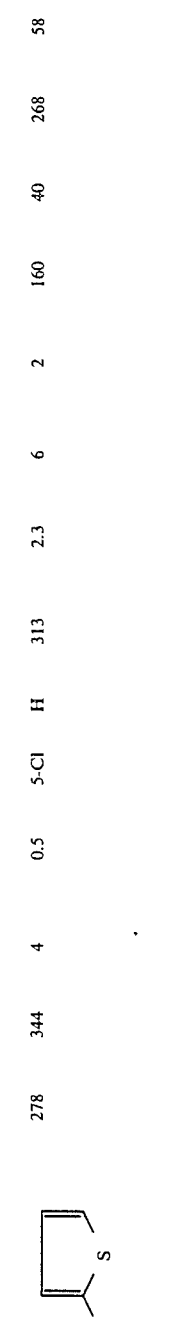 | 200 | 177 | 4 | 0.4 | 8-F | H | 250 | 4 | 5.6 | 1.4 | 180 | 35 | 312 | 87.6 | C₈₉ |
| 90 |  | 245 | 345 | 4 | 0.5 | 5-Cl | H | 312 | 3.0 | 7 | 2 | 160 | 40 | 312 | 72 | C₉₀ |
| 91 |  | 278 | 344 | 4 | 0.5 | 5-Cl | H | 313 | 2.3 | 6 | 2 | 160 | 40 | 268 | 58 | C₉₁ |

TABLE 2-continued
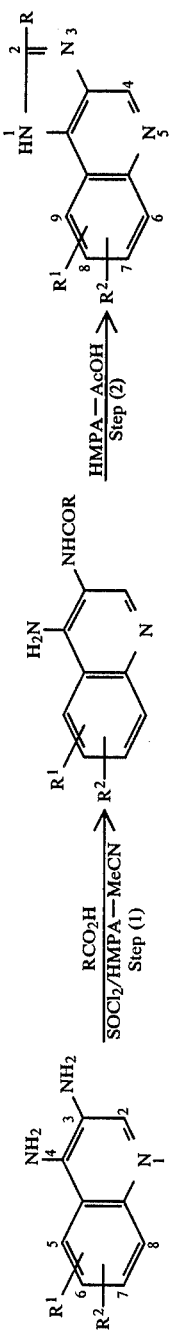
| Ex. No. | R | Step (1) | | | | | | | Step (2) | | | | Compd. C | | Compd. No. |
|---|---|---|---|---|---|---|---|---|---|---|---|---|---|---|---|
| | | RCO$_2$H (mg) | SOCl$_2$ (mg) | HMPA—MeCN (ml) | R$^1$ | R$^2$ | Compd. (mg) | Reaction time (hr) | HMPA (ml) | HMPA—AcOH (ml) | Temp. (°C.) | Reaction Time (min) | Yield (mg) | Yield (%) from Compd. A | |
| 92 | ![structure with Me, S, Me] | 309 | 331 | 4 | 0.5 | 5-Cl | H | 311 | 3.0 | 6 | 2 | 163 | 45 | 346 | 72 | C$_{92}$ |
| 93 | ![structure with Me, N—O, Me] | 315 | 283 | 5 | 0.5 | 5-F | H | 400 | 4 | 4 | 1 | 180 | 40 | 303 | 50 | C$_{93}$ |

TABLE 3

| Cmpd. No. | R¹ | R² | R | m.p. (°C.) | Appearance | Solvent for Crystallin. | Molecular Formula | Elementary Analysis (%) Up: Calcd. Down: Found ||||| 
|---|---|---|---|---|---|---|---|---|---|---|---|---|
| | | | | | | | | C | H | N | S | |
| $C_2$ | H | H |  | 296–298 | light yellow | EtOH | $C_{14}H_9N_3SCl$ | 58.85 58.86 | 2.82 3.22 | 14.71 14.40 | 11.22 11.22 | Cl 12.41 Cl 12.34 |
| $C_3$ | H | H |  | 300–301 | colorless | EtOH | $C_{16}H_{10}N_3F$ | 72.99 72.90 | 3.83 4.13 | 15.96 15.75 | | F 7.22 F 7.17 |
| $C_7$ | H | H |  | 304–305 | colorless | EtOH | $C_{14}H_9N_3S$ | 66.91 66.94 | 3.61 3.55 | 16.72 16.61 | 12.76 12.52 | |
| $C_8$ | H | H |  | 225–227 | colorless | AcOEt—n-hexane | $C_{14}H_7N_3SCl_2$ | 52.52 52.23 | 2.20 2.58 | 13.12 13.00 | 10.01 9.95 | Cl 22.14 Cl 22.05 |
| $C_9$ | H | H |  | 286–288 | colorless | EtOH | $C_{14}H_8N_3SCl$ | 58.85 58.93 | 2.82 2.88 | 14.71 14.62 | 11.22 11.44 | Cl 12.41 Cl 12.45 |
| $C_{10}$ | H | H |  | 247–249 | colorless | EtOH | $C_{16}H_{10}N_4$ | 73.16 73.34 | 4.09 4.43 | 22.75 22.54 | | |
| $C_{11}$ | H | H | | 280–282 | colorless | EtOH—AcOEt | $C_{14}H_9N_3S$ | 66.91 66.64 | 3.61 3.66 | 16.72 16.49 | 12.76 12.60 | |

TABLE 3-continued

Structure:

$$\begin{array}{c} \overset{1}{HN}-\overset{2}{C}\overset{R}{=}\overset{3}{N} \\ | \\ \text{(quinoline ring with positions 4,5,6,7,8,9; } R^1 \text{ at 8/9, } R^2 \text{ at 7)} \end{array}$$

| Cmpd. No. | R¹ | R² | R | m.p. (°C.) | Appearance | Solvent for Crystallin. | Molecular Formula | Elementary Analysis (%) Up: Calcd. Down: Found |||||
|---|---|---|---|---|---|---|---|---|---|---|---|---|
| | | | | | | | | C | H | N | S | |
| C₁₂ | H | H | 2-furyl (methyl) | 257–258 | colorless | AcOEt | C₁₄H₉N₃O | 71.48 / 71.46 | 3.86 / 3.92 | 17.86 / 17.79 | | |
| C₁₃ | H | H | 4-MeO-phenyl | 292–293 | colorless | MeOH—AcOEt | C₁₇H₁₃N₃O | 74.17 / 73.80 | 4.76 / 4.90 | 15.26 / 14.84 | | |
| C₁₄ | H | H | phenyl | 298–300 | colorless | EtOH | C₁₆H₁₁N₃ | 78.35 / 78.06 | 4.52 / 4.47 | 17.13 / 17.04 | | |
| C₁₅ | 8-Cl | H | 5-Cl-thienyl | 315–316 | colorless | MeOH—AcOEt | C₁₄H₇N₃SCl₂ · 1/10 CH₃—C(O)—OC₂H₅ | 52.57 / 52.47 | 2.39 / 2.54 | 12.77 / 12.88 | 9.74 / 9.68 | Cl 21.55 / 21.55 |
| C₁₆ | 8-Cl | H | 4-F-phenyl | 316–318 | colorless | EtOH—AcOEt | C₁₆H₉N₃ClF | 64.55 / 64.54 | 3.05 / 3.20 | 14.11 / 14.10 | | Cl 11.91 / 11.83, F 6.38 / 6.27 |
| C₁₇ | H | H | 2-furyl | 290–291(d) | colorless | MeOH—AcOEt | C₁₄H₉N₃O | 71.48 / 71.47 | 3.86 / 4.01 | 17.86 / 17.80 | | |
| C₁₈ | H | H | 4-MeS-phenyl | 325–326 | colorless | EtOH | C₁₇H₁₃N₃S | 70.08 / 70.16 | 4.50 / 4.65 | 14.42 / 14.36 | 11.00 / 10.87 | |

TABLE 3-continued

| Cmpd. No. | R$^1$ | R$^2$ | R | m.p. (°C.) | Appearance | Solvent for Crystallin. | Molecular Formula | Elementary Analysis (%) Up: Calcd. Down: Found | | | | |
|---|---|---|---|---|---|---|---|---|---|---|---|---|
| | | | | | | | | C | H | N | S | |
| C$_{19}$ | H | H | 4-AcNH-C$_6$H$_4$ | >340 | colorless | EtOH | C$_{18}$H$_{14}$N$_4$O·½H$_2$O | 69.44<br>69.47 | 4.86<br>4.93 | 18.00<br>17.86 | | |
| C$_{20}$ | H | H | 3-F-C$_6$H$_4$ | 291–293 | colorless | MeOH—AcOEt | C$_{16}$H$_{10}$N$_3$F | 72.99<br>72.62 | 3.83<br>3.88 | 15.96<br>15.83 | | F 7.22<br>F 7.28 |
| C$_{21}$ | H | H | 2-F-C$_6$H$_4$ | 259–260 | colorless | MeOH—AcOEt | C$_{16}$H$_{10}$N$_3$F | 72.99<br>72.94 | 3.83<br>4.16 | 15.96<br>15.69 | | F 7.22<br>F 7.51 |
| C$_{22}$ | H | H | 2-Cl-C$_6$H$_4$ | 199–201 | colorless | AcOEt | C$_{16}$H$_{10}$N$_3$Cl | 68.70<br>68.57 | 3.60<br>3.65 | 15.02<br>15.04 | | Cl 12.67<br>Cl 12.82 |
| C$_{23}$ | H | H | 5-Cl-thien-2-yl | 305–306 | light yellow | EtOH—AcOEt | C$_{14}$H$_8$N$_3$SCl | 58.85<br>58.58 | 2.82<br>3.16 | 14.71<br>14.43 | 11.22<br>10.95 | Cl 12.41<br>Cl 12.52 |

TABLE 3-continued

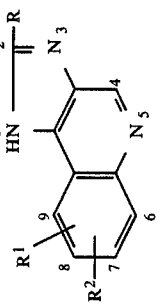

| Cmpd. No. | R[1] | R[2] | R | m.p. (°C.) | Appearance | Solvent for Crystallin. | Molecular Formula | Elementary Analysis (%) Up: Calcd. Down: Found | | | | |
|---|---|---|---|---|---|---|---|---|---|---|---|---|
| | | | | | | | | C | H | N | S | |
| C24 | H | H | ⟨MeO-phenyl⟩ | 233–235 | colorless | AcOEt | $C_{17}H_{13}N_3O$ | 74.17<br>74.02 | 4.76<br>4.78 | 15.26<br>14.97 | | |
| C25 | H | H | ⟨Me-thiophene⟩ | 283–285 | colorless | EtOH | $C_{15}H_{11}N_3S$ | 67.90<br>67.77 | 4.18<br>4.29 | 15.84<br>15.59 | 12.08<br>11.81 | |
| C26 | H | H | ⟨MeO$_2$C-phenyl⟩ | 251–253 | colorless | AcOEt | $C_{18}H_{13}N_3O_2\cdot$<br>$1/5CH_3-\overset{O}{\underset{\|}{C}}-OC_2H_5$ | 70.36<br>70.29 | 4.58<br>4.61 | 13.09<br>13.07 | | |
| C27 | H | H | ⟨difluorophenyl⟩ | 194–195 | colorless | EtOH | $C_{16}H_9N_3F_2$ | 68.33<br>68.40 | 3.23<br>3.26 | 14.94<br>15.04 | | F 13.51<br>F 13.46 |
| C28 | H | H | ⟨diMeO-phenyl⟩ | 265–267 | colorless | EtOH | $C_{18}H_{16}N_3O_2\cdot\tfrac{1}{8}H_2O$ | 70.29<br>70.26 | 5.00<br>5.07 | 13.66<br>13.66 | | |

TABLE 3-continued

| Cmpd. No. | R¹ | R² | R | m.p. (°C.) | Appearance | Solvent for Crystallin. | Molecular Formula | Elementary Analysis (%) Up: Calcd. Down: Found | | | | |
|---|---|---|---|---|---|---|---|---|---|---|---|---|
| | | | | | | | | C | H | N | S | |
| C29 | H | H | 3,5-(MeO)₂-C₆H₃ | 291–292 | colorless | EtOH | $C_{18}H_{16}N_3O_2$ | 70.81<br>71.17 | 4.95<br>4.94 | 13.76<br>13.80 | | |
| C30 | H | H | 4-O₂N-C₆H₄ | >340 | Yellow | DMF | $C_{16}H_{10}N_4O_2\cdot\frac{1}{2}H_2O$ | 65.19<br>65.48 | 3.59<br>3.74 | 19.01<br>18.91 | | |
| C31 | H | H | 2,3-F₂-C₆H₃ | 248–250 | colorless | EtOH | $C_{16}H_9N_3F_2$ | 68.33<br>68.15 | 3.23<br>3.34 | 14.94<br>14.95 | | F 13.51<br>F 13.62 |
| C32 | H | H | 2,4-F₂-C₆H₃ | 224–226 | colorless | EtOH—AcOEt | $C_{16}H_9N_3F_2$ | 68.33<br>68.63 | 3.23<br>3.47 | 14.95<br>14.99 | | F 13.51<br>F 13.72 |
| C33 | H | H | 3,4-F₂-C₆H₃ | 310–311 | colorless | EtOH—AcOEt | $C_{16}H_9N_3F_2$ | 68.33<br>68.33 | 3.23<br>3.49 | 14.94<br>14.88 | | F 13.51<br>F 13.58 |

TABLE 3-continued

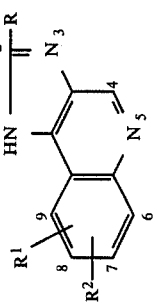

| Cmpd. No. | R¹ | R² | R | m.p. (°C.) | Appearance | Solvent for Crystallin. | Molecular Formula | Elementary Analysis (%) Up: Calcd. Down: Found ||||
|---|---|---|---|---|---|---|---|---|---|---|---|
| | | | | | | | | C | H | N | S |
| C₃₄ | H | H | Me-thiophene-Cl | 326(d) | colorless | EtOH | $C_{16}H_{10}N_3SCl$ | 60.10 / 59.74 | 3.36 / 3.63 | 14.02 / 13.71 | 10.69 / 10.61 |
| C₃₅ | 7-Cl | H | thiophene | >310 | colorless | EtOH | $C_{14}H_8N_3SCl$ | 58.85 / 58.61 | 2.82 / 3.11 | 14.71 / 14.40 | 11.22 / 11.11 |
| C₃₆ | 7-Cl | H | phenyl-F | >315 | colorless | CHCl₃—MeOH | $C_{16}H_9N_3ClF$ | 64.55 / 64.67 | 3.05 / 3.32 | 14.11 / 14.11 | Cl 11.91 / Cl 12.07 |
| C₃₇ | H | H | Me-thiophene | 295–296 | colorless | EtOH—AcOEt | $C_{16}H_{11}N_3S$ | 67.90 / 67.84 | 4.18 / 4.35 | 15.84 / 15.64 | 12.08 / 11.97 |
| C₃₈ | 7-Cl | H | Me-thiophene | 287–289 | colorless | EtOH | $C_{15}H_{10}N_3SCl$ | 60.10 / 60.00 | 3.36 / 3.50 | 14.20 / 13.96 | 10.69 / 10.60 |
| C₃₉ | 7-Cl | H | Me-thiophene | 307–308 | colorless | EtOH | $C_{15}H_{10}N_3SCl\cdot\tfrac{1}{2}H_2O$ | 59.65 / 59.78 | 3.42 / 3.59 | 13.91 / 14.03 | 10.62 / 10.20 |
| C₄₀ | 8-F | H | phenyl-F | >310 | colorless | EtOH—AcOEt | $C_{16}H_9N_3F_2$ | 68.33 / 68.20 | 3.23 / 3.48 | 14.94 / 14.92 | F 13.51 / F 13.60 |

TABLE 3-continued

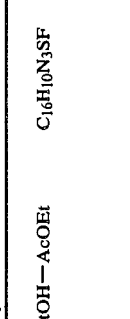

| Cmpd. No. | R¹ | R² | R | m.p. (°C.) | Appearance | Solvent for Crystallin. | Molecular Formula | Elementary Analysis (%) Up: Calcd. Down: Found | | | |
|---|---|---|---|---|---|---|---|---|---|---|---|
| | | | | | | | | C | H | N | S |
| C₄₁ | 8-F | H | 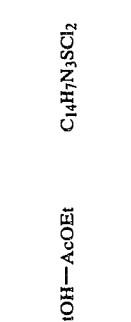 Me-thiophene-Me | 272–274 | colorless | EtOH—AcOEt | $C_{16}H_{10}N_3SF$ | 63.59 63.52 | 3.56 3.77 | 14.83 14.71 | 11.32 11.02 |
| C₄₂ | 7-Me | H | thiophene-Me | 323–326 | colorless | EtOH—AcOEt | $C_{15}H_{11}N_3S\cdot\tfrac{1}{4}H_2O$ | 67.33 67.18 | 4.24 4.51 | 15.66 15.64 | |
| C₄₃ | 7-Me | H | Me-thiophene-Me | >315 | colorless | EtOH—AcOEt | $C_{16}H_{13}N_3S$ | 68.79 68.52 | 4.69 4.91 | 15.04 14.85 | |
| C₄₄ | 7-Cl | 8-Cl | thiophene-Me | >300 | colorless | EtOH—AcOEt | $C_{14}H_7N_3SCl_2$ | 52.51 52.25 | 2.20 2.55 | 13.13 13.00 | 10.01 9.84 |
| C₄₅ | H | H | Me-isoxazole-Me | 303–304.5 | colorless | EtOH—AcOEt | $C_{14}H_{16}N_4O$ | 67.19 67.25 | 4.02 4.22 | 22.38 22.20 | |
| C₄₆ | H | H | Et-isoxazole-Me | 254–256 | colorless | AcOEt—MeOH | $C_{16}H_{12}N_4O\cdot\tfrac{1}{8}H_2O$ | 67.59 67.76 | 4.63 4.68 | 21.02 20.74 | |
| C₄₇ | 7-F | H | Et-isoxazole-Me | 309–311(d) | colorless | AcOEt—MeOH | $C_{16}H_{11}N_4OF$ | 63.82 63.58 | 3.92 4.06 | 19.84 19.74 | |

TABLE 3-continued

Structure: HN(1)-R at position with quinoline ring (N5), R¹ at 8, R² at 7, positions 6,7,8,9 on benzo ring; R = -N=C(Me)-CH=C(Me)-O- (isoxazole-like group, methyl-substituted)

| Cmpd. No. | R¹ | R² | R | m.p. (°C.) | Appearance | Solvent for Crystallin. | Molecular Formula | Elementary Analysis (%) Up: Calcd. Down: Found | | | |
|---|---|---|---|---|---|---|---|---|---|---|---|
| | | | | | | | | C | H | N | S |
| C₄₈ | 7-F | H | (Me-isoxazole) | 308–310(d) | colorless | AcOEt—MeOH | C₁₄H₉N₄OF | 62.68 / 62.46 | 3.38 / 3.50 | 20.88 / 20.67 | |
| C₄₉ | 8-F | H | (Me-isoxazole) | 293–295 | colorless | AcOEt | C₁₄H₉N₄OF·¼H₂O | 61.87 / 61.65 | 3.70 / 3.51 | 20.28 / 20.54 | |
| C₅₀ | 7-MeO | H | (Me-isoxazole) | 208–282(d) | colorless | AcOEt—MeOH | C₁₄H₁₂N₄O₂·⅛AcOEt | 63.91 / 63.69 | 4.49 / 4.44 | 19.23 / 19.25 | |
| C₅₁ | 7-MeO | H | (Me-isoxazole) | 303–305(d) | colorless | AcOEt—MeOH | C₁₅H₁₂N₄·⅛H₂O | 67.40 / 67.36 | 4.65 / 4.67 | 20.96 / 21.02 | |
| C₅₂ | 8-Cl | H | (Me-isoxazole) | 310–311(d) | light yellow | AcOEt—MeOH | C₁₄H₉N₄OCl·5/6H₂O | 55.96 / 56.08 | 3.58 / 3.72 | 18.64 / 18.57 | |
| C₅₃ | 7-Cl | H | (Me-isoxazole) | 322–325(d) | colorless | AcOEt—MeOH | C₁₄H₈N₄OClF·⅜H₂O | 53.43 / 53.40 | 2.99 / 3.26 | 17.80 / 17.68 | |

TABLE 3-continued

| Cmpd. No. | R¹ | R² | R | m.p. (°C.) | Appearance | Solvent for Crystallin. | Molecular Formula | Elementary Analysis (%) Up: Calcd. Down: Found | | | | |
|---|---|---|---|---|---|---|---|---|---|---|---|---|
| | | | | | | | | C | H | N | S | |
| C54 | 7-Cl | H | Me-isoxazole | 319–321(d) | colorless | AcOEt—MeOH | $C_{14}H_9N_4OCl\cdot CH_3OH$ | 56.87 56.62 | 4.13 4.29 | 17.68 17.54 | | Cl: 11.19 Cl: 11.07 |
| C55 | 7-CF₃ | H | Me-isoxazole | 295–297(d) | colorless | AcOEt | $C_{16}H_9N_4OF_3$ | 56.60 56.58 | 2.85 3.05 | 17.60 17.61 | | |
| C56 | 7-Cl-F | H | Me-isoxazole | 256–258 | colorless | EtOH | $C_{14}H_9N_4OCl_2$ | 52.68 52.40 | 2.53 2.62 | 17.56 17.41 | | Cl: 22.22 Cl: 22.42 |
| C57 | 6-F | H | Me-isoxazole | 308–310(d) | colorless | AcOEt—MeOH | $C_{14}H_9N_4OF$ | 62.68 62.49 | 3.38 3.63 | 20.88 20.82 | | |
| C58 | H | H | isoxazole | 271–274(d) | colorless | AcOEt | $C_{13}H_8N_4\cdot\frac{1}{8}H_2O$ | 65.47 65.41 | 3.49 3.74 | 23.49 23.28 | | |
| C59 | 7-Cl | H | isoxazole | 302–306(d) | colorless | MeOH—CHCl₃ | $C_{13}H_7N_4OCl\cdot\frac{1}{8}H_2O$ | 57.21 57.20 | 2.68 2.94 | 20.53 20.36 | | |
| C60 | 7-F | H | isoxazole | 297–299 | colorless | AcOEt—MeOH | $C_{13}H_7N_4OF\cdot 1/6H_2O$ | 60.70 60.96 | 2.87 3.17 | 21.78 21.73 | | |

TABLE 3-continued structure: HN(1)-[quinoline with positions 4,5,6,7,8,9 and N at 3,4,5]-R, with R¹ at 8, R² at 7

| Cmpd. No. | R¹ | R² | R | m.p. (°C.) | Appearance | Solvent for Crystallin. | Molecular Formula | Elementary Analysis (%) Up: Calcd. Down: Found | | | |
|---|---|---|---|---|---|---|---|---|---|---|---|
| | | | | | | | | C | H | N | S |
| C₆₁ | H | H | (3-methyl-5-methylisoxazole) | 273–274 | colorless | AcOEt | C₁₄H₉N₄O | 67.19 / 67.23 | 4.02 / 4.22 | 22.38 / 22.20 | |
| C₆₂ | 7-F | H | (3-methyl-5-methylisoxazole) | 328–330(d) | colorless | AcOEt—EtOH | C₁₄H₉N₄OF | 62.68 / 62.46 | 3.38 / 3.58 | 20.88 / 20.67 | |
| C₆₃ | H | H | (3-methyl-5-ethylisoxazole) | 268–269 | colorless | AcOEt | C₁₅H₁₂N₄O | 68.17 / 68.16 | 4.57 / 4.74 | 21.19 / 21.01 | |
| C₆₄ | 7-F | H | (3-methyl-5-ethylisoxazole) | 307–310(d) | colorless | AcOEt—EtOH | C₁₅H₁₁N₄OF | 63.82 / 63.74 | 3.92 / 4.08 | 19.84 / 19.68 | |
| C₆₅ | 8-F | H | (3-methyl-5-methylisoxazole) | 312–315(d) | colorless | AcOEt—MeOH | C₁₄H₉N₄OF | 62.68 / 62.56 | 3.38 / 3.56 | 20.88 / 20.666 | |
| C₆₆ | 7-Cl | H | (3-methyl-5-methylisoxazole) | 344–347(d) | colorless | MeOH | C₁₄H₉N₄OCl | 59.06 / 58.78 | 3.18 / 3.22 | 19.67 / 19.44 | |

TABLE 3-continued

| Cmpd. No. | R | m.p. (°C.) | Appearance | Solvent for Crystallin. | Molecular Formula | Elementary Analysis (%) Up: Calcd. Down: Found | | | |
|---|---|---|---|---|---|---|---|---|---|
| | | | | | | C | H | N | S |
| C67 | (structure: Me, S, N, Me) | 274–275 | colorless | AcOEt—EtOH | C14H10N4S.1/6H2O | 62.30 / 62.56 | 3.88 / 4.12 | 20.76 / 20.62 | |
| C68 | (structure) | 309–310(d) | colorless | AcOEt—EtOH | C14H10N4S.1/6H2O | 62.43 / 62.68 | 3.87 / 4.15 | 20.80 / 20.89 | |
| C69 | (structure) | 296–298 | colorless | MeOH | C13H9N5O | 57.98 / 58.18 | 4.12 / 3.98 | 26.01 / 25.90 | |
| C70 | (structure) | 290–293(d) | colorless | MeOH | C12H7N5S.H2O | 53.13 / 53.30 | 3.34 / 3.39 | 25.81 / 25.54 | |
| C71 | (structure) | 303–305(d) | colorless | MeOH—AcOEt | C14H10N4S | 63.13 / 63.29 | 3.78 / 3.80 | 21.03 / 20.83 | S: 11.81 / 11.69 |
| C72 | (structure) | 245–246(d) | colorless | AcOEt-hexane | C14H10N4S.½H2O | 62.61 / 62.89 | 3.85 / 4.00 | 20.86 / 20.57 | |
| C73 | (structure) | 292–294(d) | colorless | AcOEt—McOH | C13H8N4S | 61.88 / 61.94 | 3.19 / 3.30 | 22.20 / 21.97 | |

Note: R1 = H, R2 = H for all entries C67–C73.

TABLE 3-continued

| Cmpd. No. | R¹ | R² | R | m.p. (°C.) | Appearance | Solvent for Crystallin. | Molecular Formula | Elementary Analysis (%) Up: Calcd. Down: Found | | | |
|---|---|---|---|---|---|---|---|---|---|---|---|
| | | | | | | | | C | H | N | S |
| C₇₄ | H | H | (thiazole) | 242–244 | colorless | AcOEt | $C_{13}H_8N_4S.1/5H_2O$ | 61.02 61.27 | 3.31 3.57 | 21.89 21.81 | |
| C₇₅ | H | H | (N-Me pyrazole) | 276–278(d) | colorless | EtOH—AcOEt | $C_{14}H_{11}N_6.1/5H_2O$ | 66.50 66.65 | 4.54 4.73 | 27.69 27.47 | |
| C₇₆ | H | H | (N-Me imidazole) | 263–265 | colorless | EtOH—AcOEt | $C_{14}H_9N_5$ | 67.46 67.56 | 4.45 4.74 | 28.09 27.85 | |
| C₇₇ | H | H | (CH₃ oxazole) | 251–253 | colorless | EtOH—AcOEt | $C_{14}H_{10}N_4O$ | 67.19 67.29 | 4.03 4.09 | 22.39 22.13 | |
| C₇₈ | H | H | (thiazole) | 242–243 | colorless | AcOEt | $C_{13}H_8N_4S.1/5H_2I$ | 61.02 61.27 | 3.31 3.57 | 21.89 21.81 | |
| C₇₉ | 8-Cl | H | (oxazole) | 299–302(d) | light yellow | AcOEt—MeOH | $C_{13}H_7N_4OCl$ | 57.68 57.69 | 2.60 2.76 | 20.69 20.53 | |
| C₈₀ | 8-F | H | (oxazole) | 308–310(d) | colorless | MeOH—AcOEt | $C_{13}H_7N_4OF$ | 61.41 61.71 | 2.77 3.03 | 22.03 21.91 | |

TABLE 3-continued

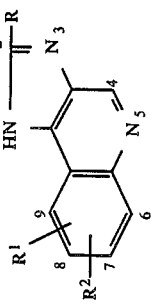

| Cmpd. No. | R¹ | R² | R | m.p. (°C.) | Appearance | Solvent for Crystallin. | Molecular Formula | Elementary Analysis (%) Up: Calcd. Down: Found | | | |
|---|---|---|---|---|---|---|---|---|---|---|---|
| | | | | | | | | C | H | N | S |
| C81 | 8-F | H | (isoxazole-Me) | 308–310.5(d) | colorless | MeOH—AcOEt | $C_{13}H_7N_4FO$ | 61.41 61.63 | 2.77 3.03 | 22.03 21.86 | |
| C82 | 8-OMe | H | (isoxazole-Me) | 279–281(d) | colorless | MeOH—AcOEt | $C_{14}H_{10}N_4O_2 \cdot \frac{1}{4}H_2O$ | 62.10 62.19 | 3.93 3.92 | 20.69 20.69 | |
| C83 | 7-F | H | (isoxazole-Me) | 316–319(d) | colorless | MeOH—AcOEt | $C_{13}H_7N_4FO \cdot \frac{1}{8}H_2O$ | 60.88 61.02 | 2.85 3.13 | 21.85 21.77 | |
| C84 | 6-F | H | (isoxazole-Me) | 329–332(d) | colorless | MeOH—CH₂Cl₂ | $C_{14}H_{10}N_4FO$ | 61.41 61.59 | 2.77 3.02 | 22.03 21.99 | |
| C85 | 7-Me | H | (isoxazole-Me) | 294–297.5(d) | colorless | AcOEt | $C_{14}H_{10}N_4O$ | 67.19 67.27 | 4.02 4.03 | 22.38 22.41 | |
| C86 | 7-CF₃ | H | (isoxazole-Me) | 324–338(d) | colorless | MeOH—AcOEt | $C_{14}H_7N_4F_3O$ | 55.27 55.43 | 2.31 2.56 | 18.41 18.40 | |

TABLE 3-continued

Structure: HN(1)—R with positions 2,3,4,5 (N), 6,7,8,9 on quinoline; R¹ at 8/9, R² at 7.

| Cmpd. No. | R¹ | R² | R | m.p. (°C.) | Appearance | Solvent for Crystallin. | Molecular Formula | Elementary Analysis (%) Up: Calcd. Down: Found | | | | |
|---|---|---|---|---|---|---|---|---|---|---|---|---|
| | | | | | | | | C | H | N | S | |
| C87 | 9-F | H | (3-methylisoxazol-5-yl) | 277–279 | colorless | MeOH—AcOEt | C₁₃H₇N₄OF | 61.41 / 61.51 | 2.77 / 3.02 | 22.03 / 21.90 | | |
| C88 | 9-F | H | (thien-2-yl) | 282–284.5(d) | colorless | MeOH—AcOEt | C₁₄H₈N₃FS | 62.44 / 62.66 | 2.99 / 3.26 | 15.50 / 15.69 | | |
| C89 | 6-F | H | (thien-2-yl) | 320–322 | colorless | EtOH | C₁₄H₈N₃SF | 62.44 / 62.25 | 2.99 / 3.22 | 15.60 / 15.36 | | |
| C90 | 9-Cl | H | (3-methylisoxazol-5-yl) | 210–212 | colorless | MeOH | C₁₃H₇N₄OCl·½CH₃OH | 56.55 / 56.69 | 3.16 / 2.97 | 19.55 / 20.03 | | Cl: 12.37 / 12.51 |
| C91 | 9-Cl | H | (thien-2-yl) | 243–245 | colorless | MeOH | C₁₄H₈N₃SCl | 58.84 / 58.79 | 2.82 / 3.02 | 14.71 / 14.86 | S: 11.22 / 10.96 | Cl: 12.41 / 12.30 |
| C92 | 9-Cl | H | (2,5-dimethylthien-3-yl) | 202–203 | colorless | MeOH | C₁₆H₁₀N₃SCl | 60.09 / 59.88 | 3.36 / 3.50 | 14.02 / 14.00 | S: 10.70 / 10.64 | Cl: 11.83 / 11.86 |
| C93 | 9-F | H | (3-methylisoxazol-5-yl, N-methyl) | 292–294 | colorless | AcOEt—MeOH | C₁₄H₉N₄FO | 62.28 / 62.83 | 3.38 / 3.52 | 20.88 / 20.84 | | |

EXAMPLE 94

2-(4-Aminophenyl)-1H-imidazo[4,5-c]quinoline $C_{94}$

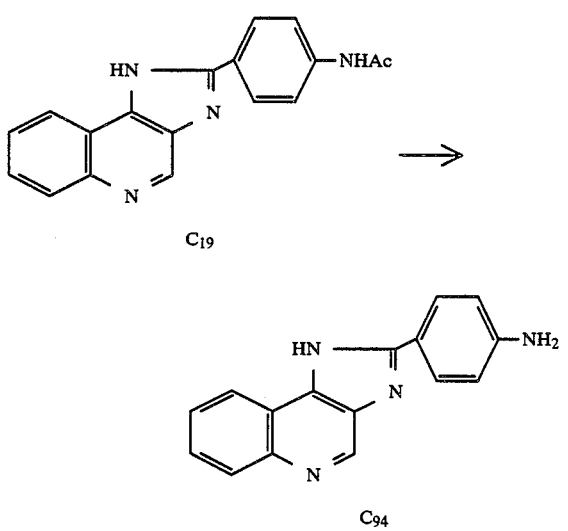

A suspension of 320 mg of 2-(4-acetylaminophenyl)-1H-imidazo[4,5-c]quinoline $C_{19}$ in 10 ml of 1N sodium hydroxide is refluxed for 1.5 hours. After the mixture is cooled and neutralized with acetic acid, the resulting white crystals are filtered, washed successively with water and ethanol, and dried to give 195 mg (71%) of $C_{94}$.

m.p. ca. 340° C. (from ethanol).

Anal. Calcd. (%) (for $C_{16}H_{12}N_4 \cdot \frac{1}{3}C_2H_5OH$): C, 73.36; H, 4.83; N, 21.06. Found (%): C, 73.44; H, 4.93; N, 20.95.

EXAMPLE 95

2-(4-methylphenyl)-1H-imidazo[4,5-c]quinoline $C_{95}$

A suspension of 326 mg of 4-methylbenzoic acid and 318 mg of 3,4-diaminoquinoline $A_1$ in 10 g of polyphosphoric acid is heated with stirring at 180° C. for 4 hours. The cooled mixture is poured into ice-water and neutralized with aqueous sodium hydroxide. The resulting solid is chromatographed on silica gel with chloroform-methanol (25:1 v/v) as eluent to give 430 mg (83%) of $C_{95}$ as white crystals.

m.p.: 326°-329° C. (dec.) (from ethanol).

Anal. Calcd. (%) (for $C_{17}H_{13}N_3 \cdot \frac{1}{3}H_2O$): C, 76.96; H, 5.19; N, 15.84. Found (%): c, 76.86; H, 4.84; N, 15.52.

EXAMPLE 96

2-(4-Chlorophenyl)-1H-imidazo[4,5-c]quinoline $C_{96}$

A suspension of 239 mg of 4-chlorobenzoic acid and 470 mg of 3,4-diaminoquinoline $A_1$ in 9 g of polyphosphoric acid is heated at 185° C. for 4 hours with stirring under nitrogen. The same work-up as described in Example 95 gives 248 g (59%) of $C_{96}$ as white crystals.

m.p. 335°-337° C. (dec.) (from ethanol).

Anal. Calcd. (%) (for $C_{16}H_{10}N_3Cl$): C, 68.70; H, 3.60; N, 15.02; Cl, 12.68. Found (%): C, 68.42; H, 3.71; N, 14.83; Cl, 12.76.

EXAMPLE 97

2-(4-Fluorophenyl)-1-methyl-1H-imidazo[4,5-c]quinoline $C_{97}$

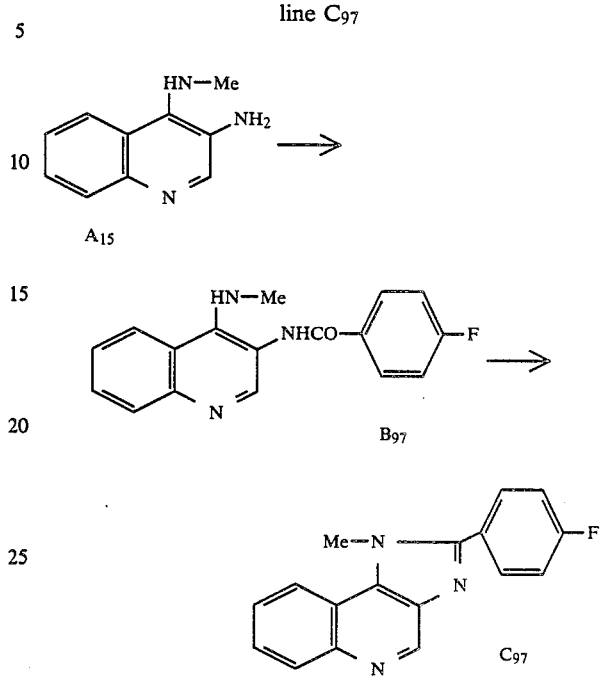

To a solution of 390 mg of 4-fluorobenzoic acid in 6 ml of anhydrous hexamethylphosphoramide and 0.6 ml of anhydrous acetonitrile is added dropwise 320 mg of thionyl chloride at $-5°$-$0°$ C. under nitrogen. After stirring at the same temperature for 30 minutes, a solution of 440 mg of 3-amino-4-methylaminoquinoline $A_{15}$ in 4 ml of anhydrous hexamethylphosphoramide is added and stirred at 0° C. for 2.5 hours. The same work-up as described in Example 1 gives 750 mg of $B_{97}$ as a white solid. It is dissolved in 10 ml of acetic acid and refluxed for 1 hour. The mixture is concentrated under reduced pressure and the residue is shaken with ethyl acetate-saturated aqueous sodium bicarbonate. The organic layer is separated, washed successively with water and aqueous sodium chloride, and dried. The solvent is evaporated and the residue is crystallized from n-hexane to give 610 mg (87%) of $C_{97}$ as white crystals.

m.p.: 185°-187° C. (from ethyl acetate).

Anal. Calcd. (%) (for $C_{17}H_{12}N_3F$): C, 73.63; H, 4.36; N, 15.15; F, 6.85. Found (%): C, 73.73; H, 4.36; N, 15.15; F, 6.77.

EXAMPLE 98

1-Ethyl-2-(5-methylthien-2-yl)-1H-imidazo[4,5-c]quinoline $C_{98}$

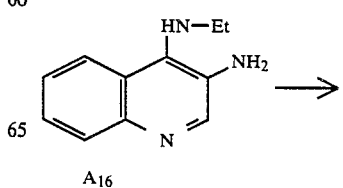

-continued

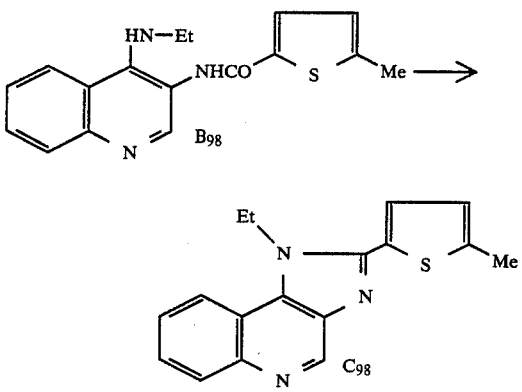

To a solution of 270 mg of 5-methylthiophene-2-carboxylic acid in 5 ml of anhydrous hexamethylphosphoramide and 0.5 ml of anhydrous acetonitrile is added dropwise 215 mg of thionyl chloride at $-5°-0°$ C. under nitrogen. After stirring at the same temperature for 30 minutes, a solution of 320 mg of 3-amino-4-ethylaminoquinoline $A_{16}$ in 0.5 ml of anhydrous hexamethylphosphoramide is added and stirred at $0°-5°$ C. for 3 hours. The same work-up as described in Example 1 gives 510 mg of $B_{98}$ as a white solid. It is suspended in 10 ml of acetic acid and refluxed for 1 hour. The mixture is concentrated and the residue is shaken with ethyl acetate-saturated aqueous sodium bicarbonate. The organic layer is separated, washed successively with water and saturated aqueous sodium chloride, and dried. The solvent is evaporated and the residue is chromatographed on silica gel with chloroform-methanol (20:1 v/v) as eluent to give 380 mg (76%) of $C_{98}$ as colorless crystals.

m.p.: 205°-206° C. (dec.) (from ethyl acetate).

Anal. Calcd. (%) (for $C_{17}H_{15}N_3S$): C, 69.60; H, 5.15; N, 14.32; S, 10.93. Found (%): C, 69.66; H, 4.96; N, 14.30; S, 10.88.

EXAMPLE 99

2-(4-Methyloxazol-5-yl)-1H-imidazo[4,5-c]quinoline $C_{99}$

To a solution of 300 mg of 4-methyloxazole-5-carboxylic acid in 4 ml of hexamethylphosphoramide and 0.4 ml of acetonitrile is added 268 mg of thionyl chloride at $-5°-0°$ C. under nitrogen. After stirring at the same temperature for 30 minutes, 340 mg of 3,4-diaminoquinoline $A_1$ is added and stirred at $0°-5°$ C. for 3 hours. The mixture is diluted with ice-water and neutralized with saturated aqueous sodium bicarbonate. The resulting solid is filtered and washed with water to give 425 mg of 4-amino-3-(4-methylisoxazole-5-ylcarbonylamino)quinoline as crude crystals. It is suspended in 12 ml of Dowtherm A (Dow Chemimical Co.) and refluxed for 2.5 hours. The cooled mixture is diluted with 50 ml of n-hexane and the resulting solid is collected by filtration. It is chromatographed on silica gel with dichloromethane-methanol (20:1 v/v) as eluent to yield a crude solid which is recrystallized from ethyl acetate-methanol, giving 297 mg of $C_{99}$ as pale yellow crystals.

m.p. 289°-292° C. (dec.).

Anal. Calcd. (%) (for $C_{14}H_{10}N_4O.\frac{1}{2}H_2O$): C, 66.59; H, 4.09; N, 22.19. Found (%): C, 66.86; H, 4.18; N, 21.98.

EXAMPLE 100

2-(3-Methylisoxazol-5-yl)-1H-imidazo[4,5-c]quinoline hydrochloride $C_{100}$

To an ethanolic solution of 300 mg of 2-(3-methylisoxazol-5-yl)-1H-imidazo[4,5-c]quinoline $C_{45}$ is added ethanolic hydrogen chloride at room temperature. The mixture is evaporated and the residue is washed with acetone to give $C_{100}$ as crystals melting at 248.5°-252° C. (dec.).

Anal. Calcd. (%) (for $C_{14}H_{11}N_4OCl.\frac{1}{3}H_2O$): C, 57.45; H, 4.02; N, 19.14; Cl, 12.11. Found (%): C, 57.64; H, 4.27; N, 18.90; Cl, 12.23.

EXAMPLE 101

3-Methanesulfonyl-2-(3-methylisoxazol-5-yl)-3H-imidazo[4,5-c]quinoline $C_{101}$ To a solution of 300 mg of 2-(3-methylisoxazol-5-yl)-1H-imidazo[4,5-c]quinoline $C_{45}$ in 20 ml of tetrahydrofuran is added 50 mg of 60% sodium hydride in mineral oil and stirred at 75° C. for 2 hours under nitrogen. To the cooled mixture is added dropwise 180 mg of methanesulfonyl chloride and stirred at $0°-5°$ C. for 2 hours. The mixture is concentrated under reduced pressure and the residue is poured into ice-water. The resulting solid is collected by filtration and chromatographed on silica gel with dichloromethane-methanol (50:1 v/v) as eluent, yielding 159 mg (40%) of $C_{101}$ as white crystals.

m.p. 167.5°-169° C. (dec.) (from ethyl acetate).

Anal. Calcd. (%) (for $C_{15}H_{12}N_4O_3S$): C, 54.86; N, 3.68; N, 17.06. Found (%): C, 54.95; H, 3.97; N, 16.79.

EXAMPLE 102

1-Methyl-2-(3-methylisoxazol-5-yl)-1H-imidazo[4,5-c]quinoline $C_{102}$

To a solution of 245 mg of 3-methylisoxazole-5-carboxylic acid in 20 ml of hexamethylphosphoramide and 0.4 ml of acetonitrile is added 226 mg of thionyl chloride at $-5°-0°$ C. After stirring at the same temperature for 30 minutes, 330 mg of 3-amino-4-methylaminoquinoline $A_{15}$ is added and stirred at $0°-5°$ C. for 5 hours. The mixture is diluted with 50 ml of ice-water and neutralized with saturated aqueous sodium bicarbonate. The resulting solid is filtered and washed with water to give 361 mg (67%) of 4-methylamino-3-[(3-methylisoxazole-5-ylcarbonyl)amino]quinoline. It is suspended in 4 ml of hexamethylphosphoramide and 1 ml of acetic acid and stirred at 180° C. (bath temperature) for 40 minutes. The cooled mixture is poured into ice-water and neutralized with aqueous sodium bicarbonate. The resulting solid is filtered, washed with water and chromatographed on silica gel with dichloromethane-methanol (25:1 v/v) as eluent. The product obtained is recrystallized from dichloromethane-methanol to give 294 mg of $C_{102}$ as white crystals melting at 281°-284° C. (dec.).

Anal. Calcd. (%) (for $C_{15}H_{12}N_4O$) : C, 68.17; H, 4.57; N, 21.19. Found (%): C, 68.29; N, 4.57; N, 21.21.

NMR (CDCl$_3$-CD$_3$OD): δ2.46(s, 3H), 4.57(s, 3H), 6.99(s, 1H), 7.6-8.7(m, 4H), 9.23(s, 1H).

EXAMPLE 103

2-(Fluorophenyl)-3-methyl-3H-imidazo[4,5-c]quinoline $C_{103}$,
2-(4-Fluorophenyl)-1-methyl-1H-imidazo[4,5-c]quinoline $C_{97}$ and
2-(4-Fluorophenyl)-5-methyl-5H-imidazo[4,5-c]quinoline $C_{104}$

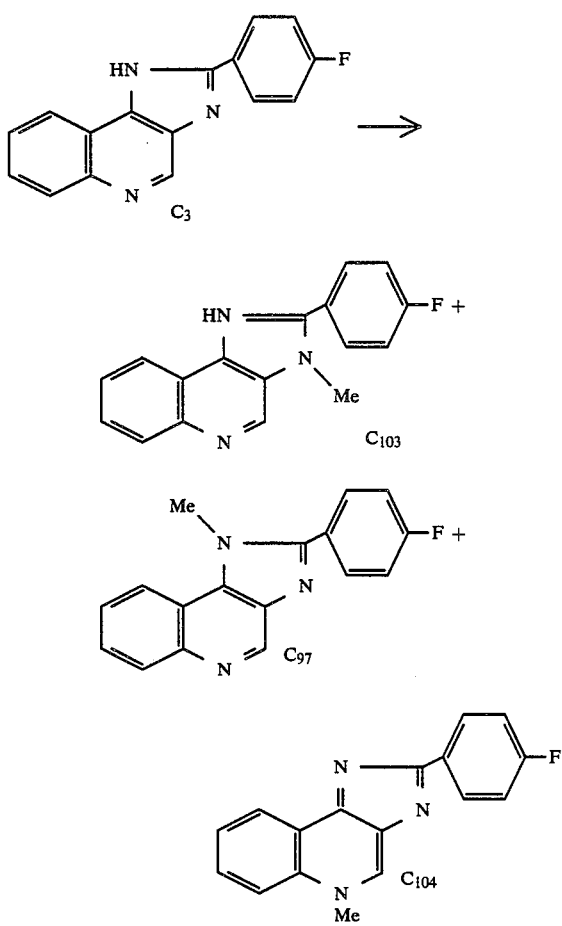

To a solution of sodium ethoxide (prepared from 70 mg of metallic sodium and 10 ml of anhydrous ethanol) is added 520 mg of 2-(4-fluorophenyl)-1H-imidazo[4,5-c]quinoline $C_3$ at room temperature under nitrogen and stirred for 5 minutes. To the mixture is added 0.5 ml of methyl iodide and stirred at 50° C. for 1 hour. The mixture is poured into ice-water and extracted with ethyl acetate. The extract is washed with water and dried. Evaporation of the solvent gives a residue which is chromatographed on silica gel with chloroform-methanol (30:1 v/v) as eluent. The fractions containing the compound with an Rf=0.35 are combined and evaporated to give 90 mg (16%) of 3-methyl derivative $C_{103}$ as colorless crystals.

m.p. 168°–170° C. (ethyl acetate-n-hexane).

Anal. Calcd. (%) (for $C_{17}H_{12}N_3F$): C, 73.63; H, 4.36; N, 15.15; F, 6.85. Found (%): C, 73.86; H, 4.56; N, 15.13; F, 6.86.

NMR (CDCl$_3$): δ 4.02(s, 2H), 7.17–8.77(m, 8H), 9.10(s, 1H)

Then evaporation of the combined fractions containing the product with an Rf=0.27 yields 60 mg (11%) of 1-methyl derivative $C_{97}$ which is identical with the compound obtained in Example 97.

Lastly the combined fractions containing the compound with an Rf=0.12 is evaporated to give 340 mg (62%) of 5-methyl derivative $C_{104}$ as colorless crystals.

m.p. 277°–278° C. (from ethyl acetate-methanol).

Anal. Cald. (%) (for $C_{17}H_{12}N_3F$): C, 73.63; N, 4.36; N, 15.15; F, 6.85. Found (%): C, 73.64; H, 4.36; N, 15.05; F, 6.76.

NMR (CDCl$_3$): δ 4.23(s, 3H), 7.03–8.93(m, 8H), 8.56(s, 1H).

EXAMPLE 104

3-Methyl-2-(3-methylisoxazol-5-yl)-3H-imidazo[4,5-c]quinoline $C_{105}$,
1-Methyl-2-(3-methylisoxazol-5-yl)-1H-imidazo[4,5-c]quinoline $C_{102}$ and
5-Methyl-2-(3-methylisoxazol-5-yl)-5H-imidazo[4,5-c]quiniline $C_{106}$ To a solution of 450 mg of 2-(3-methylisoxazol-5-yl)-1H-imidazo[4,5-c]quinoline $C_{45}$ in 39 ml of tetrahydrofuran is added 80 mg of 60% sodium hydride in mineral oil and stirred at 60° C. for 1.5 hours under nitrogen. To the cooled mixture is added dropwise 385 mg of methyl iodide in 2 ml of tetrahydrofuran at 0°–5° C. After stirring at 0°–5° C. for 30 minutes and then at 40° C. for 4 hours, the mixture is evaporated and the residue is chromatographed on silica gel with dichloromethane-methanol (50:1 v/v) as eluent, to give 58 mg (12%) of 3-methyl derivative $C_{105}$ as white crystals.

m.p. 179.5°–182° C. (from ethyl acetate).

Anal. Calcd. (%) (for $C_{15}H_{12}N_4O.\frac{1}{4}H_2O$): C, 67.03; H, 4.69; N, 20.84. Found (%): C, 67.16; N, 4.98; N, 20.62.

NMR(CDCl$_3$—CD$_3$OD): δ 2.46(s, 3H), 4.35(s, 3H), 7.13(s, 1H), 7.6–8.7 (m, 4H), 9.13 (s, 1H).

The further elution with the same solvent yields 42 mg (9%) of 1-methyl derivative $C_{102}$ which is identical with the compound described in Example 102.

Then the eluate with the dichloromethane-methanol (25:1 v/v) affords 322 mg (68%) of 5-methyl derivative $C_{106}$ as white crystals.

m.p.: 308°–309° C. (dec.) (from ethyl acetate-methanol).

Anal. Calcd. (%) (for $C_{15}H_{12}N_4O$): C, 68.17; H, 4.57; N, 21.19. Found (%): C, 68.14; H, 4.76; N, 21.12.

NMR (CDCl$_3$—CD$_3$OD): δ 2.42(s, 3H), 4.40(s, 3H), 6.99(s, 1H), 7.6–8.9 (m, 4H), 9.07(s, 1H).

EXAMPLE 105

2-(4-Fluorophenyl)-7-methyl-1H-imidazo[4,5-c]thieno[2,3-b]pyridine $F_1$

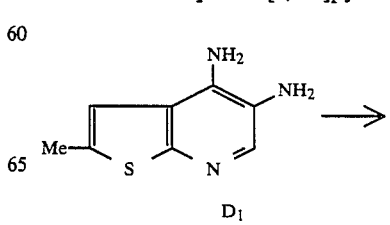

-continued

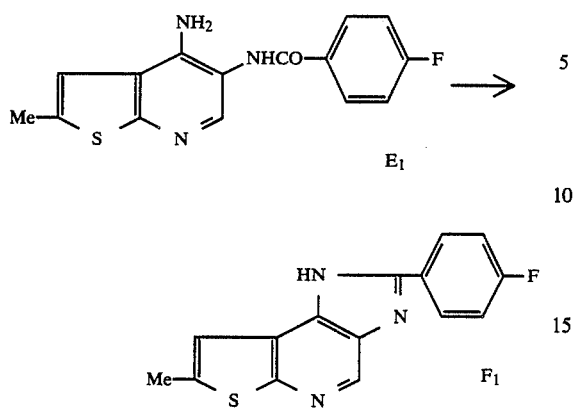

To a solution of 308 mg of 4-fluorobenzoic acid in 5 ml of anhydrous hexamethylphosphoramide and 0.5 ml of anhydrous acetonitrile is added dropwise 250 mg of thionyl chloride at −5°–0° C. under nitrogen. After stirring at the same temperature for 30 minutes, 358 mg of diaminothienopyridine $D_1$ is added and stirred at 0°–5° C. for 3 hours. The mixture is diluted with ice-water and neutralized with saturated aqueous sodium bicarbonate. The resulting crystals are filtered, washed with water and dried to yield 630 mg of 4-amino-2-methyl-5-(4-fluorobenzoylamino)thieno[2,3-b]pyridine $E_1$. It is suspended in 15 ml of polyphosphoric acid and heated at 140° C. with stirring under nitrogen. The cooled mixture is poured into ice-water and neutralized with aqueous sodium hydroxide. The product is extracted with ethyl acetate and the extract is washed with water, dried and evaporated. The residue is chromatographed on silica gel with chloroform-methanol (25:1 v/v) as eluent to afford 457 mg (81%) of $F_1$ as colorless crystals.

m.p.: 313°–316° C. (from ethanol).

Anal. Calcd. (%) (for $C_{15}H_{10}N_3SF$): C, 63.58; H, 3.55; N, 14.83; S, 11.31. Found (%): C, 63.32; H, 3.79; N, 14.61; S, 11.09.

EXAMPLE 106

2-(Thien-2-yl)-7-methyl-1H-imidazo[4,5-d]thieno[2,3-b]pyridine $F_2$

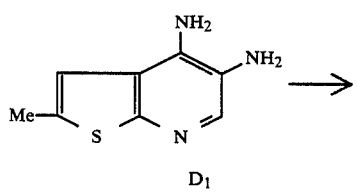

-continued

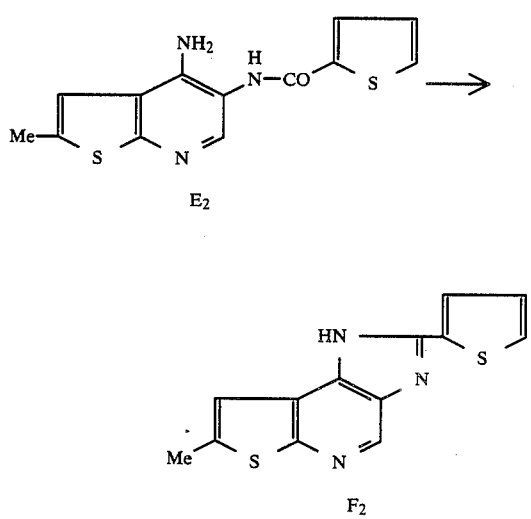

To a solution of 212 mg of thiophene-2-carboxylic acid in 4 ml hexamethylphosphoramide and 0.4 ml of acetonitrile is added dropwise 188 mg of thionyl chloride at −5°–0° C. under nitrogen. After stirring at 0°–5° C. for 30 minutes, 269 mg of diaminothienopyridine $D_1$ is added and stirred at 0°–5° C. for 3 hours. The same work-up as described in Example 105 gives 403 mg of $E_2$ as crude crystals. It is suspended in 20 ml of Dowtherm A (Dow Chemical Co.) and refluxed for 3 hours under nitrogen. The cooled mixture is diluted with n-hexane and the resulting crystals are filtered. It is chromatographed on silica gel with chloroform-methanol (25:1 v/v) as eluent to give 286 mg (70%) of $F_2$ as colorless crystals.

m.p.: 284°–287° C. (from methanol-ethyl acetate).

Anal. Cald. (%) (for $C_{13}H_9N_3S_2$): C, 57.54; H, 3.34; N, 15.48; S, 23.68. Found (%): C, 57.46; H, 3.60, N, 15.39; S, 23.67.

EXAMPLE 107–114

According to the method illustrated by Example 106, Compounds $F_3$–$F_{10}$ are obtained under the conditions shown in Table 4. Table 5 shows the physical properties of these compounds.

TABLE 4
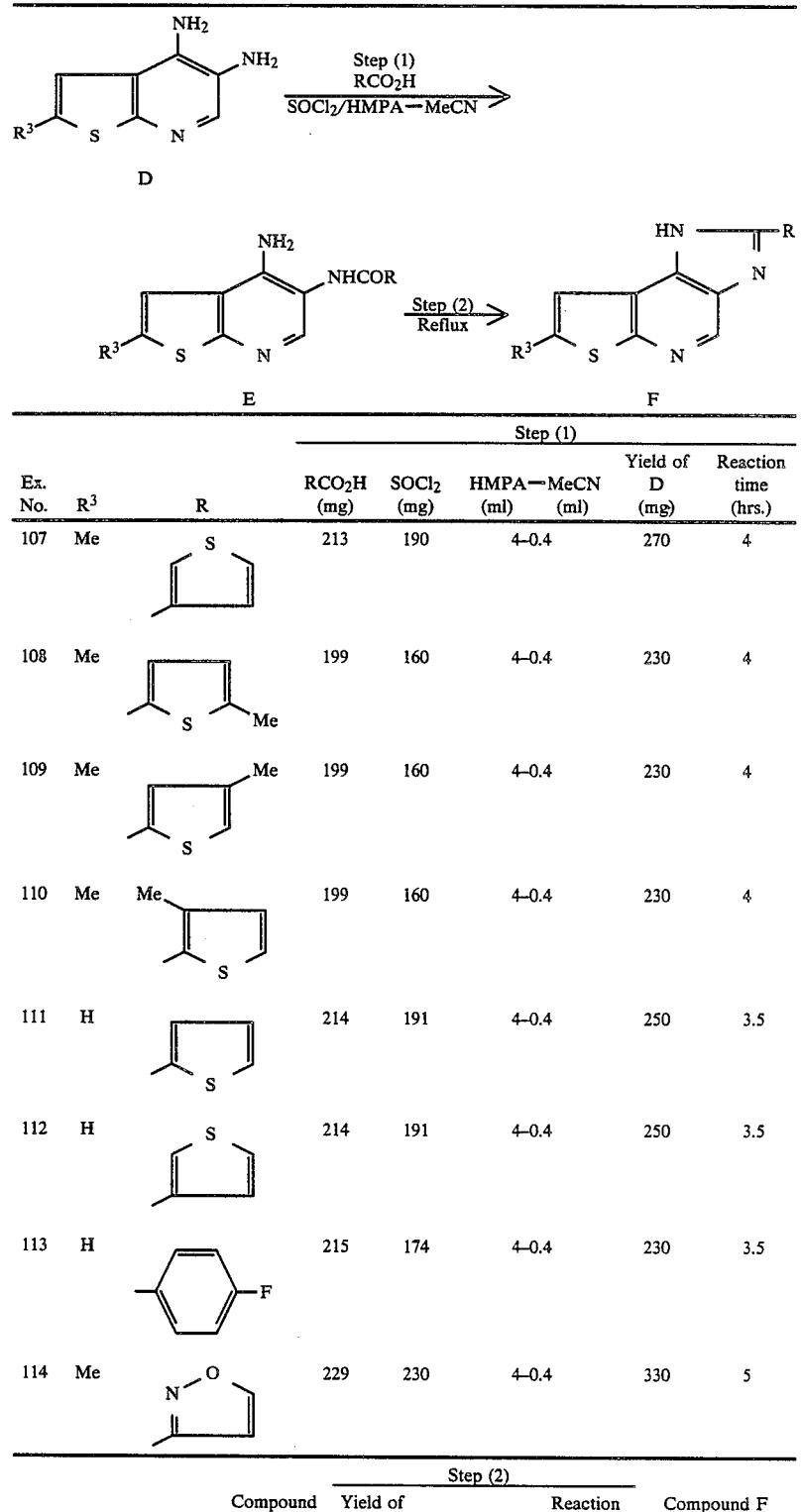
| Ex. No. | R³ | R | Step (1) RCO₂H (mg) | SOCl₂ (mg) | HMPA (ml) | MeCN (ml) | Yield of D (mg) | Reaction time (hrs.) |
|---|---|---|---|---|---|---|---|---|
| 107 | Me | 2-thienyl | 213 | 190 | 4 | 0.4 | 270 | 4 |
| 108 | Me | 2,5-dimethyl-thien-3-yl | 199 | 160 | 4 | 0.4 | 230 | 4 |
| 109 | Me | 3-methyl-thien-5-yl | 199 | 160 | 4 | 0.4 | 230 | 4 |
| 110 | Me | 2,3-dimethyl-thien-5-yl | 199 | 160 | 4 | 0.4 | 230 | 4 |
| 111 | H | 2-thienyl | 214 | 191 | 4 | 0.4 | 250 | 3.5 |
| 112 | H | 3-thienyl | 214 | 191 | 4 | 0.4 | 250 | 3.5 |
| 113 | H | 4-fluorophenyl | 215 | 174 | 4 | 0.4 | 230 | 3.5 |
| 114 | Me | 3-methylisoxazol-5-yl | 229 | 230 | 4 | 0.4 | 330 | 5 |
| Ex. No. | Compound E (mg) | Step (2) Yield of E (mg) | Dowtherm A (ml) | Reaction time (hrs.) | Compound F Yields (mg) | Compd. No. |
|---|---|---|---|---|---|---|
| 107 | 390 | 370 | 7.4 | 2 | 310 | F₃ |
| 108 | 375 | 350 | 7 | 3 | 310 | F₄ |
| 109 | 372 | 350 | 7 | 3.5 | 305 | F₅ |
| 110 | 355 | 330 | 6.6 | 16 | 250 | F₆ |
| 111 | 387 | 370 | 7.4 | 2 | 315 | F₇ |
| 112 | 378 | 350 | 7 | 2 | 300 | F₈ |
| 113 | 300 | 280 | 5.6 | 2 | 240 | F₉ |

TABLE 4-continued

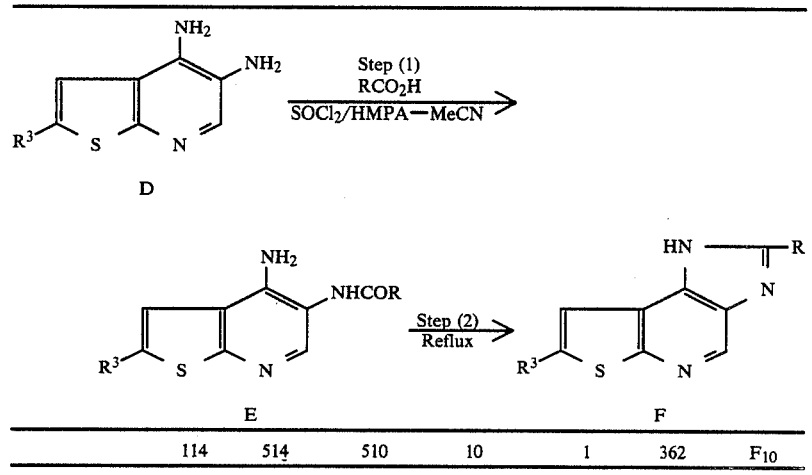

| E | | | | F | |
|---|---|---|---|---|---|
| 114 | 514 | 510 | 10 | 1 | 362 F₁₀ |

TABLE 5

F

HN—R
 ‖
 N

R³—[thieno-pyridine]

| Compd. No. | R³ | R | m.p. (°C.) | Appearance | Solvent for crystalln. | Molecular Formula | Elementary Analysis (%) Up (Calcd.). Down (Found) | | |
|---|---|---|---|---|---|---|---|---|---|
| | | | | | | | C | H | N |
| F₃ | Me | (thiophene) | 295–296 | colorless | MeOH—AcOEt | $C_{13}H_9N_3S_2$ | 57.54 57.44 | 3.34 3.61 | 15.48 15.46 |
| F₄ | Me | Me-thiophene-Me | 277–278 | colorless | EtOH—Et₂O | $C_{14}H_{11}N_3S_2 \cdot \frac{1}{2}H_2O$ | 58.46 58.49 | 3.94 4.12 | 14.16 14.56 |
| F₅ | Me | Me-thiophene | 268–270 | colorless | EtOH—Et₂O | $C_{14}H_{11}N_3S_2$ | 58.92 58.82 | 3.88 3.99 | 14.72 14.66 |
| F₆ | Me | Me-thiophene | 263–266 | colorless | EtOH—Et₂O | $C_{14}H_{11}N_3S_2$ | 58.92 58.73 | 3.88 4.11 | 14.72 14.81 |
| F₇ | H | (thiophene) | 290–293 | colorless | AcOEt—n-hexane | $C_{12}H_7N_3S_2 \cdot \frac{1}{4}AcOEt \cdot \frac{1}{3}H_2O$ | 54.72 54.83 | 3.41 3.61 | 14.73 14.59 |
| F₈ | H | (thiophene) | 277–279 | colorless | AcOEt—n-hexane | $C_{12}H_7N_3S_2 \cdot \frac{1}{8}AcOEt$ | 55.94 55.60 | 3.00 3.23 | 15.65 15.59 |
| F₉ | H | 4-F-C₆H₄ | 307–310 | colorless | AcOEt | $C_{14}H_8N_3SF \cdot \frac{1}{8}AcOEt$ | 62.13 62.32 | 3.23 3.35 | 14.99 15.25 |

TABLE 5-continued

F

| Compd. No. | R³ | R | m.p. (°C.) | Appearance | Solvent for crystalln. | Molecular Formula | Elementary Analysis (%) Up (Calcd.). Down (Found) | | |
|---|---|---|---|---|---|---|---|---|---|
| | | | | | | | C | H | N |
| F₁₀ | Me | (isoxazole) | 297–299 | colorless | AcOEt—MeOH | $C_{12}H_8N_4OS$ | 56.23 55.99 | 3.14 3.35 | 21.86 21.70 |

EXAMPLE 115

2-Phenyl-1H-imidazo[4,5-d]thieno[3,4-b]pyridine H₁

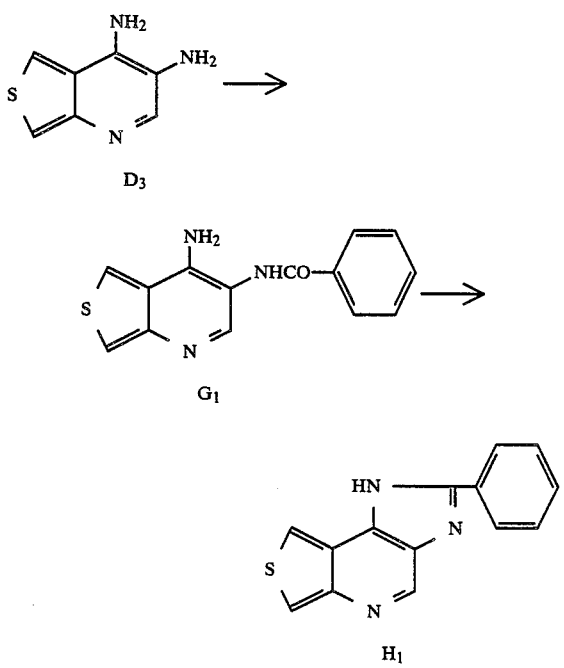

To a solution of 187 mg of benzoic acid in 5 ml of anhydrous hexamethylphosphoramide and 0.5 ml of anhydrous acetonitrile is added dropwise 174 mg of thionyl chloride at 0° C. under nitrogen. After stirring at 0° C. for 30 minutes, 239 mg of diaminothienopyridine D₃ is added and stirred for 3 hours. The mixture is diluted with ice-water and neutralized with aqueous sodium bicarbonate. The resulting crystals are filtered, washed with water and dried to give 280 mg of G₁. It is suspended in 4.2 ml of hexamethylphosphoramide and 1.1 ml of acetic acid, and heated at 170° C. for 30 minutes. The cooled mixture is diluted with ice-water and extracted with ethyl acetate, and the extract is washed with water and dried. After the solvent is evaporated, the residue is chromatographed on silica gel with chloroform-methanol (50:2 v/v) to give 170 mg (51%) of H₁ as colorless crystals.

m.p. 308°–312° C. (dec.) (from ethyl acetate-methanol).

Anal. Calcd. (%) (for $C_{14}H_9N_3S.\frac{1}{3}H_2O$): C, 65.35; H, 3.79; N, 16.33. Found (%): C, 65.29; H, 3.73; N, 16.13.

EXAMPLE 116

2-(4-Fluorophenyl)-1H-imidazo[4,5-d]thieno[3,4-b]pyridine H₂

According to the method illustrated by Example 115, 240 mg (50%) of H₂ is obtained from 281 mg of 4-fluorobenzoic acid and 300 mg of diaminothienopyridine D₃.

m.p.: 302°–305° C. (from methanol-ethyl acetate).

Anal. Calcd. (%) (for $C_{14}H_8N_3SF$): C, 62.44; H, 2.99; N, 15.60. Found (%): C, 62.23; H, 3.26; N, 15.28.

EXAMPLE 117

2-(5-Chlorothien-2-yl)-1H-imidazo[4,5-d]thieno[3,4-b]pyridine H₃

According to the method illustrated by Example 115, 259 mg of H₃ is obtained from 325 mg of 5-chlorothiophene-2-carboxylic acid and 300 mg of diaminothienopyridine D₃.

m.p.: 301°–304° C. (dec.).

Anal. Calcd. (%) (for $C_{12}H_6N_3ClS_2$): C, 49.39; H, 2.07; N, 14.40. Found (%): C, 49.09; H, 2.17; N, 14.16.

EXAMPLE 118

2-(4-Methoxylphenyl)-1H-imidazo[4,5-d]thieno[3,2-b]pyridine K₁

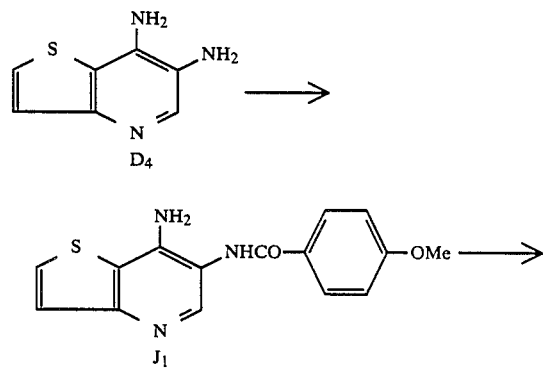

-continued

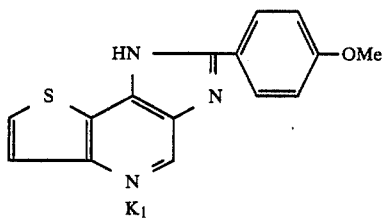

To a solution of 233 mg of 4-methoxybenzoic acid in 4 ml of hexamethylphosphoramide and 0.4 ml of acetonitrile is added 174 mg of thionyl chloride at 0° C. under nitrogen. After stirring at 0° C. for 30 minutes, 230 mg of diaminothienopyridine $D_4$ is added and stirred at 0° C. for 4 hours. The mixture is diluted with ice-water and neutralized with aqueous sodium bicarbonate. The resulting crystals are filtered, washed with water and dried to yield 348 mg (84%) of $J_1$. The mixture of $J_1$ and 6.6 ml of Dowtherm A (Dow Chemical Co.) is refluxed for 2 hours. The cooled mixture is diluted with n-hexane and allowed to stand to give 300 mg (95%) of $K_1$ as colorless crystals.

m.p.: 285°–287° C. (from ethyl acetate-methanol).

Anal. Calcd. (%) (for $C_{15}H_{11}N_3OS.1/5CH_3COOC_2H_5$): C, 63.48; H, 4.25; N, 14.06. Found (%): C, 63.20; H, 4.38; N, 13.86.

EXAMPLE 119–123

According to the method illustrated by Example 118, Compounds $K_2$–$K_6$ are prepared under the conditions shown in Table 6. Table 7 shows the physical properties of these compounds.

TABLE 6

| Example No. | R | Step (1) | | | | | | Step (2) | | | Compound K | |
|---|---|---|---|---|---|---|---|---|---|---|---|---|
| | | $RCO_2H$ (mg) | $SOCl_2$ (mg) | HMPA—MeCN (ml) (ml) | Yield of $D_4$ (mg) | Reaction time (hr.) | Compound J (mg) | Yield of J (mg) | Dowtherm A (ml) | Reaction time (hr.) | Yield (mg) | Compd. No. |
| 119 | —C₆H₄—Cl | 239 | 174 | 4–0.4 | 230 | 4.0 | 365 | 350 | 7 | 1.5 | 320 | $K_2$ |
| 120 | —C₆H₄—F | 308 | 250 | 6–0.6 | 330 | 3.0 | 475 | 400 | 8 | 1.5 | 347 | $K_3$ |
| 121 | —C₆H₅ | 268 | 250 | 6.6–0.7 | 330 | 3.0 | 458 | 440 | 9 | 1.5 | 373 | $K_4$ |
| 122 | —(2-thienyl) | 282 | 250 | 6–0.6 | 330 | 3.5 | 510 | 500 | 10 | 2 | 438 | $K_5$ |
| 123 | —(5-chloro-2-thienyl) | 260 | 181 | 4–0.4 | 240 | 3.5 | 373 | 350 | 7 | 2 | 310 | $K_6$ |

TABLE 7

| Compound No. | R | m.p. (°C.) | Appearance | Solvent for crystalln. | Molecular Formrula | Elementary Analysis (%) Up (Calcd.). Down (Found) C | H | N |
|---|---|---|---|---|---|---|---|---|
| $K_2$ | 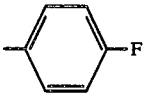 -Cl | 334–337 | colorless | MeOH—AcOEt | $C_{14}H_8N_3ClS \cdot \frac{1}{4}H_2O$ | 57.93<br>58.11 | 2.95<br>3.20 | 14.48<br>14.35 |
| $K_3$ |  -F | 272–278 | colorless | AcOEt | $C_{14}H_8N_3SF \cdot \frac{1}{4}H_2O$ | 61.41<br>61.70 | 3.13<br>3.41 | 15.35<br>14.99 |
| $K_4$ | 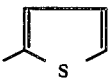 | 288–293 | colorless | MeOH—AcOEt | $C_{14}H_9N_3S$ | 66.91<br>66.66 | 3.60<br>3.86 | 16.72<br>16.59 |
| $K_5$ | thienyl | 281–285 | colorless | MeOH—AcOEt | $C_{12}H_7N_3ClS_2 \cdot 1/6H_2O$ | 55.36<br>55.51 | 2.84<br>3.03 | 16.14<br>15.86 |
| $K_6$ | chlorothienyl | 224–228 | colorless | MeOH—AcOEt | $C_{12}H_6N_3ClS_2 \cdot \frac{1}{4}CH_3OH$ | 49.07<br>49.03 | 2.35<br>2.64 | 14.01<br>14.06 |

3,4-Diaminoquinolines

The starting 3,4-diaminoquinolines are prepared by sequential chlorination, amination and reduction of 3-nitro-4-hydroxyquinolines according to literature [G. B. Bachman et al., *J. Am. Chem. Soc.*, 69,365 (1947) and A. R. Surrey et al., *J. Am. Chem. Soc.*, 73,2413 (1951)].

The following table shows their melting points.

| Comp. No. | $R_1$ | $R_2$ | mp (°C.) |
|---|---|---|---|
| $A_1$ | H | H | 168–170 (dec.) |
| $A_2$ | 6-Cl | H | 206–209 (dec.) |
| $A_3$ | 7-Cl | H | 193–195 (dec.) |
| $A_4$ | 6-F | H | 196–198 (dec.) |
| $A_5$ | 7-Me | H | 155–158 |
| $A_6$ | 6-Cl | 7-Cl | 250–253 (dec.) |
| $A_7$ | 7-F | H | 185–188 (dec.) |
| $A_8$ | 7-MeO | H | 136–139 (dec.) |
| $A_9$ | 7-CF$_4$ | H | 179–181 (dec.) |
| $A_{10}$ | 6-F | 7-Cl | 249–252 (dec.) |
| $A_{11}$ | 5-Cl | 7-Cl | 200–203 (dec.) |
| $A_{12}$ | 5-Cl | H | 157–159 |
| $A_{13}$ | 8-F | H | 167–169 (dec.) |
| $A_{14}$ | 5-F | H | 168–169.5 (dec.) |

REFERENTIAL EXAMPLE 1

3-Amino-4-methylaminoquinoiline $A_{15}$

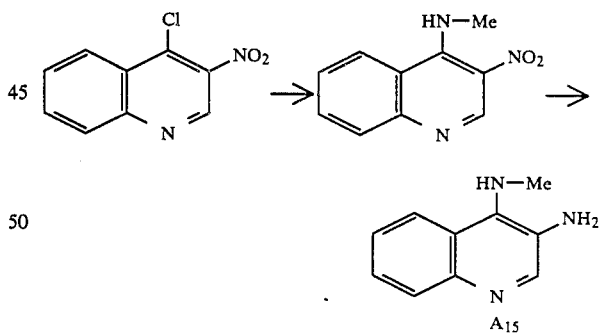

To a suspension of 2.0 g of 4-chloro-3-nitroquinoline in 20 ml of dry ethanol is added 15 ml of 30% methylamine in ethanol. The mixture is stirred at room temperature for 30 minutes and concentrated in vacuo. The residue is triturated with excess water. The resulting crystals are collected by filtration and washed repeatedly with water. The crystals are dried over phosphorus pentoxide in vacuo to afford 1.82 g (93%) of 4-methylamino-3-nitroquinoline.

An analytical sample is recrystallized from ethyl acetate to give yellow crystals melting at 172°–173° C.

Anal. Calcd. (%) (for $C_{10}H_9N_3O_2$): C, 59.11; H, 4.46; N, 20.67. Found (%): C, 59.33; H, 4.59; N, 20.67.

A suspension of 1.7 g of 4-methylamino-3-nitroquinoline in 75 ml of ethanol is hydrogenated in the presence of 300 mg of 10% palladium on carbon at atmospheric pressure. After hydrogen absorption is complete, the catalyst is removed by filtration and the filtrate is concentrated in vacuo. The residue is purified by column chromatography on silica gel. Elution with chloroform-methanol (2:1 v/v) affords 600 mg (41%) of 3-amino-4-methylaminoquinoline $A_{15}$ as an oil.

NMR (CD$_3$OD): δ 3.05(s, 3H), 7.17–7.50(m, 2H), 7.60–8.15(m, 2H), 8.38(s, 1H).

REFERENTIAL EXAMPLE 2

3-Amino-4-ethylaminoquinoline $A_{16}$

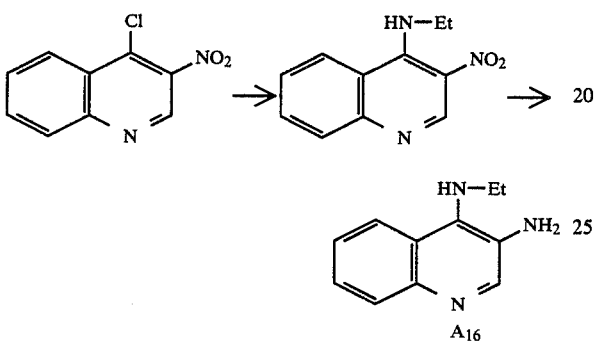

To a stirred suspension of 1.40 g of 4-chloro-3-nitroquinoline in 30 ml of dry ethanol is introduced excess amount of gaseous ethylamine at room temperature for 3 hours. Treatment of the reaction mixture as in Example 98 yielded 1.41 g (97%) of 4-ethylamino-3-nitroquinoline. Recrystallization from the ethyl acetate-n-hexane affords yellow crystals melting at 151°–152° C.

Anal. Calcd. (%) (for C$_{11}$H$_{11}$N$_3$O$_2$): C, 60.82; H, 5.10; N, 19.34. Found (%): C, 60.93; H, 5.07; N, 19.27.

A suspension of 1.34 g of 4-ethylamino-3-nitroquinoline in 40 ml of ethanol is hydrogenated in the presence of 10% palladium on carbon according to the procedure of Referential Example 1, followed by purification to give 0.95 g (82%) of 3-amino-4-ethylaminoquinoline $A_{16}$ as an oil.

NMR (CD$_3$OD): δ1.24(t,3H), 3.35(q,2H), 7.33–7.63(m,2H), 7.77–8.03(m,2H), 8.30(s,1H).

REFERENTIAL EXAMPLE 3

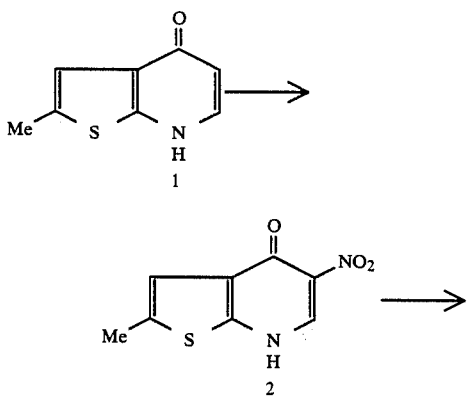

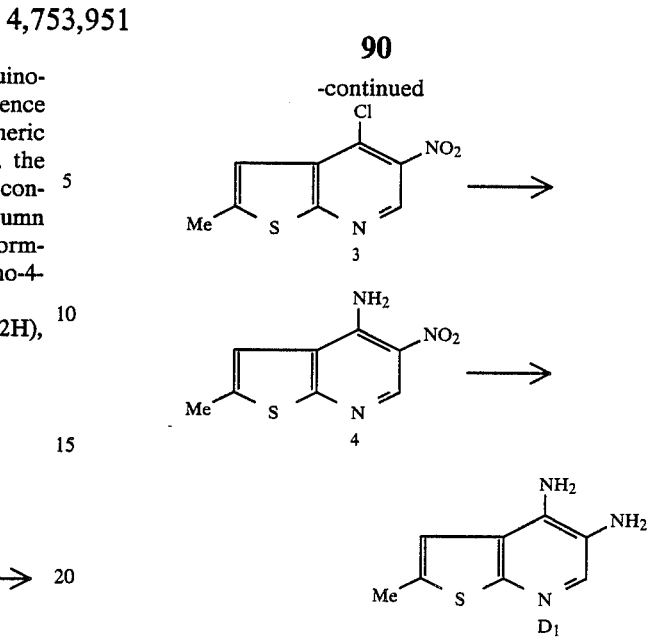

(1) 5-Nitro-2-methylthieno[2,3-b]pyridin-4(7H)-one 2

To a solution of 1.65 g of 2-methylthieno[2,3-b]pyridin-4(7H)-one 1 in 45 ml of acetic acid is added dropwise a solution of 1.24 g of concentrated nitric acid (d=1.38) in 5 ml of acetic acid at 110° C. The mixture is heated with stirring at the same temperature for 10 minutes and left on cooling. The resulting crystals are collected by filtration and washed with ethyl acetate to give 1.07 g (51%) of Compound 2 as pale yellow crystals melting at 280°–282° C. (dec.).

Anal. Calcd. (%) (for C$_8$H$_6$N$_2$O$_3$S): C, 45.71; H, 2.87; N, 13.32; S, 15.25. Found (%): C, 45.64; H, 3.42; N, 13.20; S, 15.20.

(2) 4-Chloro-5-nitro-2-methylthieno[2,3-b]pyridine 3

A mixture of 2.26 g of 5-nitro-2-methylthieno[2,3-b]pyridine-4(7H)-one 2 and 10 ml of phosphorus oxychloride is refluxed for 1 hour. The reaction mixture is concentrated to dryness in vacuo and the residue is taken up on ethyl acetate. The organic phase is dried over magnesium sulfate and treated with activated charcoal. The mixture is filtered and the solvent is evaporated in vacuo. The crude product is recrystallized from ethyl acetate-n-hexane to give 1.90 g (68%) of Compound 3 as colorless crystals melting at 96°–98° C.

Anal. Calcd. (%) (for C$_8$H$_5$N$_2$O$_2$SCl): C, 42.02; H, 2.20; N, 12.25; S, 14.02. Found (%): C, 41.92; H, 2.48; N, 12.16; S, 14.12.

(3) 4-Amino-5-nitro-2-methylthieno[2,3-b]pyridine 4

To a stirred solution of 1.60 g of 4-chloro-5-nitro-2-methylthieno[2,3-b]pyridine 3 in 50 ml of 2-propanol is introduced excess amount of anhydrous ammonia at 55° C. during 3 hours. The reaction mixture is concentrated in vacuo. The residue is washed with ether and suspended in 7 ml of 1N sodium hydroxide solution with stirring. The resulting crystals are collected by filtration and washed with water and a small amount of ethanol to yield 1.37 g (93%) of Compound 4 as orange crystals melting at 238°–240° C.

Anal. Calcd. (%) (for C$_8$H$_7$N$_3$O$_2$S): C, 45.92; H, 3.37; N, 20.08; S, 15.32. Found (%): C, 45.71; H, 3.40; N, 19.84; S, 15.44.

(4) 4,5-Diamino-2-methylthieno[2,3-b]pyridine $D_1$

A suspension of 1.25 g of 4-amino-5-nitro-2-methylthieno[2,3-b]pyridine is hydrogenated under atmospheric pressure at room temperature in the presence of 360 mg of 10% palladium carbon for 2 hours. After removal of catalyst, the filtrate is concentrated and the residue is triturated with chloroform to give 866 mg (81%) of Compound $D_1$ as colorless crystals melting at 204°–209° C.

Anal. Calcd. (%) (for $C_8H_9N_3S$): C, 53.60; H, 5.06; N, 23.44; S, 17.88. Found (%): C, 53.56; H, 5.11; N, 23.24; S, 18.01.

REFERENTIAL EXAMPLE 4

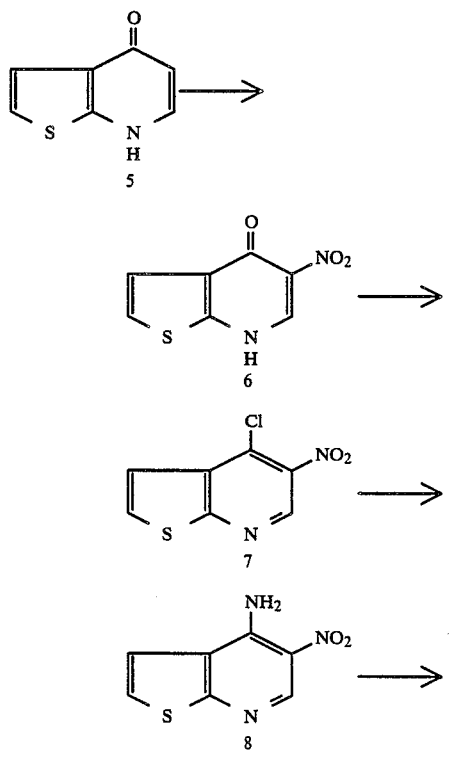

(1) 5-Nitrothieno[2,3-b]pyridin-4(7H)-one 6

To a solution of 3.4 g of thieno[2,3-b]pyridin-4(7H)-one 5 in 105 ml of propionic acid is added 2.79 g of concentrated nitric acid (d=1.38) at 100° C., and then the mixture is stirred at 130° C. (bath temperature) for 1 hour. After cooling the reaction mixture, the resulting precipitate is collected by filtration and washed successively with water, methanol and acetone to afford 3.4 g (77%) of Compound 6 as pale yellow crytals melting at 288°–291° C.

(2) 4-Chloro-5-nitrothieno[2,3-b]pyridine 7

A mixture of 3.4 g of 5-nitrothieno[2,3-b]pyridin-4(7H)-one 6 and 34 ml of phosphorus oxychloride is heated at 115° C. (bath temperature) for 1 hour and evaporated to dryness in vacuo. The residue is taken up in chloroform and washed with water. The organic phase is dried over magnesium sulfate and concentrated in vacuo. The residue is purified by column chromatography on silica gel. Elution with dichloromethane-ether (50:1 v/v) affords 3.51 g (94%) of Compound 7 as crystals melting at 110°–113° C.

(3) 4-Amino-5-nitrothieno[2,3-b]pyridine 8

To a stirred suspension of 3.35 g of 4-chloro-5-nitrothieno[2,3-b]pyridine 7 in 160 ml of 2-propanol is introduced excess amount of anhydrous ammonia at 45°–50° C. during 4 hours. After removal of the solvent, the residue is suspended in water. The solid is washed with water and cold ether, affording 2.65 g (87%) of Compound 8 as crystals. Recrystallization from methanol-ether gives a pure sample melting at 227°–228.5° C.

(4) 4,5-Diaminothieno[2,3-b]pyridine $D_2$

A mixture of 2.57 g of 4-amino-5-nitrothieno[2,3-b]pyridine 8 and 11.1 g of stannous chloride in 240 ml of ethanol is stirred at 75° C. for 3 hours. The reaction mixture is treated with activated charcoal and filtered. After concentration of the filtrate, the residue is taken up in ethyl acetate and suspended in 185 ml of 5% aqueous sodium bicarbonate. The organic layer is extracted with dilute hydrochloric acid. The aqueous layer is treated with activated charcoal and filtered. The filtrate is basified to pH=10 with 10% sodium hydroxide and extracted with ethyl acetate. The extract is dried over magnesium sulfate and evaporated in vacuo. The residue is recrystallized from ethyl acetate-ether to afford 1.65 g (76%) of Compound $D_2$ as pale yellow crystals melting at 159°–160.5° C.

Anal. Calcd. (%) (for $C_7H_7N_3S \cdot \frac{1}{2}H_2O$): C, 50.20; H, 4.36; N, 25.09. Found (%): C, 50.54; H, 4.24; N, 24.95.

REFERENTIAL EXAMPLE 5

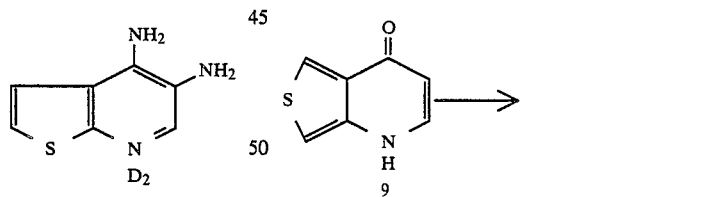

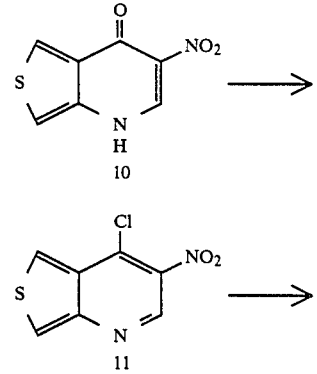

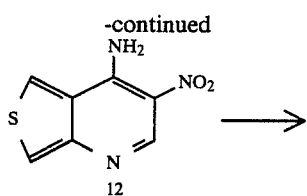

(1) 3-Nitrothieno[3,4-b]pyridin-4(1H)-one 10

To a suspension of 4.00 g of thieno[3,4-b]pyridin-4(1H)-one 9 in 120 ml of acetic acid is added 3.00 g of nitric acid (d=1.38). The reaction mixture is stirred at 70° C. for 3 minutes and cooled to room temperature. The resulting crystals are collected by filtration, and then washed with water and methanol-ether, affording 2.51 g (48%) of Compound 10. An analytical sample is recrystallized from dimethylsulfoxide-methanol to give yellow crystals melting at 329°–332° C.

Anal. Calcd. (%) (for C$_7$H$_4$N$_2$O$_3$S): C, 42.85; H, 2.05; N, 14.27. Found (%): C, 42.75; H, 2.30; N, 14.13.

(2) 4-Chloro-3-nitrothieno[3,4-b]pyridine 11

A mixture of 3.00 g of 3-nitrothieno[3,4-b]pyridin-4(1H)-one 10 and 9 ml of phosphorous oxychloride is stirred at 105° C. (bath temperature) for 1 hour and evaporated to dryness in vacuo. The residue is taken up in chloroform and washed with aqueous ammonia and water. The organic phase is dried over magnesium sulfate and evaporated. The residue is purified by column chromatography on silica gel. Elution with dichloromethane-ether (50:1 v/v) affords 2.02 g (60%) of Compound 11. Recrystallization from ether-petroleum ether affords colorless crystals melting at 139°–140° C.

Anal. Calcd. (%) (for C$_7$H$_3$N$_2$O$_2$ClS.⅓H$_2$O): C, 38.77; H, 1.51; N, 12.92. Found (%): C, 38.60; H, 1.55; N, 12.79.

(3) 4-Amino-3-nitrothieno[3,4-b]pyridine 12

To a stirred suspension of 1.25 g of 4-chloro-3-nitrothieno[3,4-b]pyridine 11 in 37 ml of 2-propanol is introduced anhydrous ammonia at room temperature during 3 hours. The mixture is concentrated in vacuo and the residue is suspended in water with stirring. The crystals are collected by filtration, washed with water and dried to give 1.09 g (96%) of Compound 12. An analytical sample is recrystallized from chloroform-methanol, giving yellow crystals melting at 307°–309° C.

Anal. Calcd. (%) (for C$_7$H$_5$N$_3$O$_2$S): C, 43.07; H, 2.58; N, 21.52. Found (%): C, 42.93; H, 2.69; N, 21.36.

(4) 3,4-Diamino[3,4-b]pyridine D$_3$

A mixture of 620 mg of 4-amino-3-nitrothieno[3,4-b]pyridine and 3.59 g of stannous chloride dihydrate in 50 ml of ethanol is stirred at 70° C. for 1 hour. After evaporation of the solvent in vacuo, the residue is partitioned between ethyl acetate and aqueous sodium bicarbonate. The resulting solid is filtered off and washed with ethyl acetate. The combined extracts are dried and evaporated in vacuo. The residue is purified by column chromatography on neutral alumina. Elution with chloroform-methanol (20:1 v/v) affords 490 mg (93%) of Compound D$_3$, which is recrystallized from ether-methanol to afford colorless crystals melting at 140°–144° C.

Anal. Calcd. (%) (C$_7$H$_7$N$_3$S.⅜H$_2$O): C, 47.44; H, 4.74; N, 23.71. Found (%): C, 47.68; H, 4.85; N, 23.24.

REFERENTIAL EXAMPLE 6

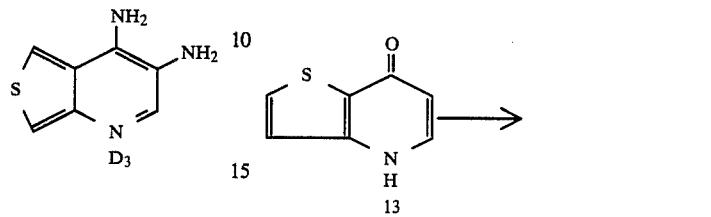

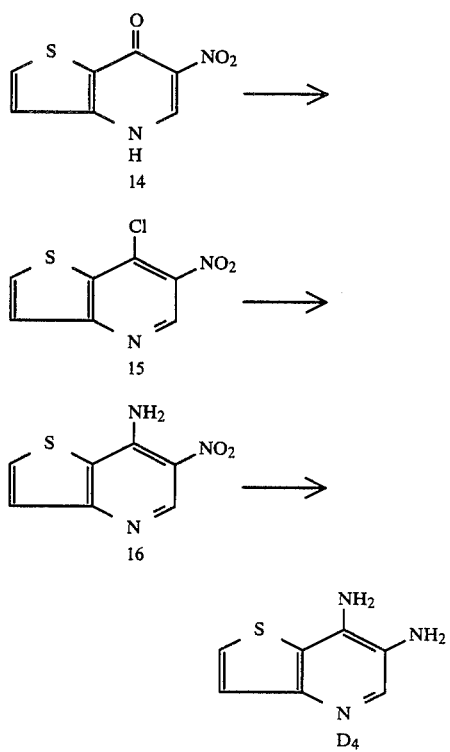

(1) 6-Nitrothieno[3,2-b]pyridin-7(4H)-one 14

To a solution of 3.1 g of thieno[3,2-b]pyridin-7(4H)-one 13 in 90 ml of propionic acid is added 1.5 ml of fuming nitric acid at 110° C. with stirring and the mixture is refluxed for 1 hour. The cooled mixture is diluted with 50 ml of ether and the resulting crystals are collected by filtration, washed with water and ether-methanol, and dried to give 3.13 g (78%) of Compound 14. Recrystallization from dimethyl sulfoxide-methanol affords colorless crystals melting at 328°–331° C. (dec.).

Anal. Calcd. (%) (for C$_7$H$_4$N$_2$O$_3$S): C, 42.85; H, 2.05; N, 14.27. Found (%): C. 42.88; H, 2.17; N, 14.21.

(2) 7-Chloro-6-nitrothieno]3,2-b]pyridin-7(4H)-one 15

A mixture of 2.7 g of 6-nitrothieno[3,2-b]pyridin-7(4H)-one 14 and 30 ml of phosphorous oxychloride is stirred at 115° C. for 1 hour. The reaction mixture is evaporated to dryness in vacuo. The residue is taken up in dichloromethane, washed successively with aqueous ammonia and water, and then dried over magnesium sulfate. The solvent is removed in vacuo and the crude crystals are purified by column chromatography on silica gel. Elution with dichloromethane-ether (50:1 v/v) affords 2.64 g (90%) of Compound 15. Recystallization from ether gives colorless crystals melting at 124°–125.5° C.

Anal. Calcd. (%) (for $C_7H_3N_2O_2ClS$): C, 39.17; H, 1.40; N, 13.05. Found (%): C, 38.96; H, 1.70; N, 12.92.

(3) 7-Amino-6-nitrothieno[3,2-b]pyridine 16

To a suspension of 2.55 g of 7-chloro-6-nitrothieno[3,2-b]pyridine 15 in 130 ml of 2-propanol is introduced excess anhydrous ammonia at 45° C. (bath temperature) during 4 hours and the mixture is evaporated in vacuo. The residue is suspended in water, collected by filtration, and then washed with water and ether to give 2.30 g (99%) of Compound 16. An analytical sample is recrystallized from chloroform methanol, affording yellow crystals melting at 266°–268.5° C.

Anal. Calcd. (%) (for $C_7H_5N_3O_2S$): C, 43.07; H, 2.58; N, 21.52. Found (%): C, 43.02; H, 2.76; N, 21.46.

(4) 6,7-Diaminothieno[3,2-b]pyridine $D_4$

A mixture of 2.3 g of 7-amino-6-nitrothieno[3,2-b]pyridine 16 and 12.5 g of stannous chloride dihydrate in 160 ml of ethanol is heated with stirring at 70° C. for 3 hours. The mixture is evaporated in vacuo and the residue was partitioned between ethyl acetate and aqueous sodium bicarbonate. The resulting solid is filtered off and washed with ethyl acetate. The combined extracts are dried and evaporated in vacuo. The residue is purified by column chromatography on silica gel. Elution with chloroform-methanol (10:1 v/v) affords 1.91 g (97%) of Compound $D_4$, which is recrystallized from methanol-ether to give colorless crystals melting at 157°–159° C.

Anal. Calcd. (%) (for $C_7H_7N_3S\cdot\frac{1}{4}H_2O$): C, 49.54; H, 4.45; N, 24.76. Found (%): C, 49.79; H, 4.35; N, 24.43.

PREPARATION 2-(3-methylisoxazol-5-yl)-1H-imidazol[4,5-c]quinoline: 10 mg
Wheat starch: 48 mg
Magnesium stearate: 2 mg The above components are mixed with each other to prepare a capsule.

EFFECT OF THE INVENTION

The compounds of the present invention show high affinity to a benzodiazepine receptor. The drugs bound to this receptor are classified as three groups according to the difference of the efficacy. Thus, agonists can be utilized as anxiolytics or anticonvulsants, antagonists can be agents for treating benzodiazepine intoxication and accidental supernumerary uptake, and inverse agonists are expected as psychostimulants.

Experiments for assessing biological activities of the compounds of the present invention are shown below; the number of the test compound nearly corresponds to the number used in Examples and Tables respectively.

EXPERIMENT 1

Binding Test to Benzodiazepine Receptor

This test was carried out in the modified mehtod of Möhler et al. Science, 198, 849–851 (1977).

Receptor preparation was provided from the cerebral cortex of Wistar rats (male, 11 to 13 weeks age). Inhibitory action of the test compound on the specific binding of tritium labeled diazepam to the receptor was evaluated as follows. 2nM tritium labeled diazepam and an aqueous solution of the test compound at 5 or 6 concentrations were incubated with the receptor preparation at 0° C. for 6 minutes. The 50% inhibitory concentration ($IC_{50}$) was measured by the concentration-response curve.

The inhibitory constant (Ki) was calculated according to the following equation, in which Kd is the dissociation constant of the tritium labeled diazepam and L is the concentration of the labeled ligand.

$$Ki = \frac{IC_{50}}{1 + L/Kd}$$

| Compound No. | Ki (nM) | Compound No. | Ki (nM) |
|---|---|---|---|
| $C_2$ | 0.97 | $C_{58}$ | 0.525 |
| $C_3$ | 15.8 | $C_{59}$ | 1.23 |
| $C_{13}$ | 8.73 | $C_{60}$ | 0.495 |
| $C_{20}$ | 27.7 | $C_{61}$ | 0.661 |
| $C_{21}$ | 1.80 | $C_{67}$ | 2.07 |
| $C_{27}$ | 1.88 | $C_{68}$ | 1.19 |
| $C_{35}$ | 19.5 | $C_{70}$ | 5.40 |
| $C_{38}$ | 15.6 | $C_{71}$ | 4.57 |
| $C_{45}$ | 0.582 | $F_2$ | 31.8 |
| $C_{46}$ | 0.97 | $F_7$ | 725 |
| $C_{48}$ | 0.907 | $K_5$ | 10.1 |
| $C_{49}$ | 0.237 | | |

Experiment 2

Antagonism of Pentyleneterazole-Induced Convulsion

Agonistic activity was evaluated in this test. Groups of 8–16 male mice were challenged with a dose of 125 mg/kg, s.c. of pentylenetetrazole immediately after intravenous injection of the test compound. The dose required to prevent tonic convulsion and death in 50% of the animal during a 2-h observation period was calculated by the probit method.

| Compound No. | $ED_{50}$ (mg/Kg) |
|---|---|
| $C_2$ | 15.97 |
| $C_3$ | 2.31 |
| $C_{13}$ | 4.61 |
| $C_{20}$ | 3.90 |
| $C_{21}$ | 2.05 |
| $C_{27}$ | 1.41 |
| $C_{38}$ | 8.52 |
| $C_{45}$ | 0.71 |
| $C_{46}$ | 1.20 |
| $C_{48}$ | 0.59 |
| $C_{49}$ | 0.32 |
| $C_{59}$ | 3.01 |
| $C_{61}$ | 0.74 |

EXPERIMENT 3

Potentiation of Pentylenetetrazole-Induced Convulsion

Inverse agonist activity was evaluated in this test. Groups of 8–16 mice were challenged with a dose of 90 mg/kg. s.c. of pentylenetetrazole (a subconvulsive dose) immidiately after intravenous injection of the test compound. The dose required to produce tonic convulsion and death in 50% of the animals during a 2-h observation period was calculated by the probit method.

| Compound No. | ED$_{50}$ (mg/Kg) |
| --- | --- |
| C$_{35}$ | 1.76 |
| C$_{58}$ | 1.65 |
| C$_{71}$ | 4.18 |
| F$_2$ | 0.13 |
| K$_5$ | 0.54 |
| F$_7$ | 0.50 |

EXPERIMENT 4

Traction Test

The modified method of Courvoisier et al. (in "Psychotropic Drugs", ed. by S. Garattini & R. Ducrot. p 373. Elsevier Publishing Co., Amsterdam, 1957) was employed. Groups of 10 mice were made to hang onto a horizontal metal wire (diameter: 1 mm) by grasping and holding with their forepaws 30 minutes after oral administration of the test compound, and the number of mice gripping the wire with hindpaws within 10 sec was counted. The ED$_{50}$ was calculated by the probit method.

EXPERIMENT 5

Anticonflict Test

The modified method of Geller and Seifter (Psychopharmacol, 1, 482, 1960) was employed. Groups of 5 or more male Wistar rats with well-established conflict behavior were used. A dose was determined as positive when the numbuer of electric shocks (punishment) exceeded more than 12 during a 1 hour observation period starting 30 minutes after oral administration of the test compound. The ED$_{50}$ was calculated by the probit method.

| Compound No. | Anti-conflict activity ED$_{50}$ (mg/kg) | Traction Test ED$_{50}$ (mg/kg) |
| --- | --- | --- |
| C$_{45}$ | 2.68 | >200 |
| C$_{48}$ | 1.80 | >200 |
| C$_{49}$ | 1.19 | >200 |
| Diazepam | 1.05 | 5.06 |

The pharmacological activities described above suggest that the dissociation of anxiolytic action and muscle relaxation action, both being specific to drugs of benzodiazepine type, was achieved. Thus, the compound of the present invention can be an anxiolytic drug not accompanied with a side effect such as dizziness.

What we claim is:

1. A compound of the formula:

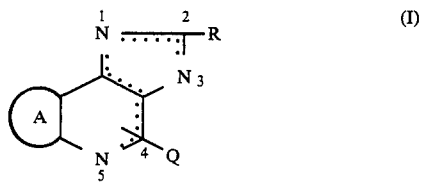

where

R is pyridyl or a 5-membered heterocyclic groiup selected from the group consisting of an isoxazolyl, isothiazolyl, pyrazolyl, oxazolyl, thiazolyl, imidazolyl, thiadiazolyl, oxadiazolyl, thienyl or furyl group optionally substituted by one or two members selected from the group consisting of halogen, C$_1$-C$_5$ alkyl and C$_1$-C$_5$ alkoxy, Q is hydrogen, C$_1$-C$_5$ alkyl, C$_1$-C$_{10}$ acyl, C$_1$-C$_5$ alkylsulfonyl or C$_6$-C$_{10}$ arylsulfonyl,

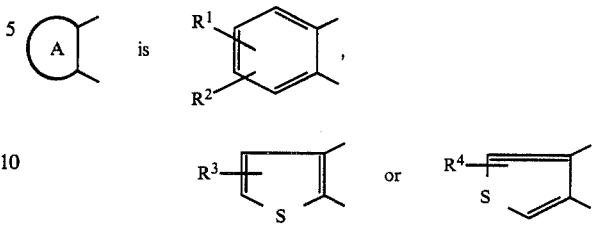

R$^1$, R$^2$, R$^3$ and R$^4$ each is hydrogen, halogen, C$_1$-C$_5$ alkyl, C$_1$-C$_5$ alkoxy or C$_1$-C$_5$ haloalkyl, Q is present on the nitrogen atom of the 1, 3 or 5-position, and the dotted line indicates the presence of three double bonds at the position of 2, 3; 3a, 3b; 4, 5/1, 3b; 2, 3; 3a, 4/or 1, 2; 3a, 3b; 4, 5 or its pharmaceutically acceptable acid addition salt.

2. A compound according to claim 1, in which

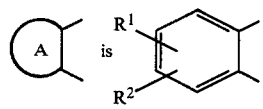

3. A compound according to claim 2, in which R is said 5-membered heterocyclic group optionally substituted by one or two members selected from the group consisting of halogen, C$_1$-C$_5$ alkyl and C$_1$-C$_5$ alkoxy.

4. A compound according to claim 3, in which the 5-membered heterocyclic group is 2-thienyl.

5. A compound according to claim 3, in which the 5-membered heterocyclic group is 3-methyl-5-isoxazolyl.

6. A compound according to claim 4, namely 7-chloro-2-(2-thienyl)-1H-imidazo[4,5-c]quinoline.

7. A compound according to claim 5, namely 2-(3-methylisoxazol-5-yl)-1H-imidazo[4,5-c]quinoline.

8. A compound according to claim 5, namely 7-fluoro-2-(3-methylisoxazol-5-yl)-1H-imidazo[4,5-c]quinoline.

9. A compound according to claim 5, namely 8-fluoro-2-(3-methylisoxazol-5-yl)-1H-imidazo[4,5-c]quinoline.

10. A compound according to claim 1, wherein R is an isoxazolyl, isothiazolyl, pyrazolyl, oxazolyl, thiazolyl, imidazolyl, thiadiazolyl, oxadiazolyl, thienyl, furyl or pyridyl group.

11. A pharmaceutical composition comprising a psychotropically effective amount of a compound according to claim 1 and one or more pharmaceutically acceptable carriers, diluent and/or excipients.

12. A method for treating psychotropic disorders which comprises administering an effective amount of the composition of claim 10 to a patient suffering from a psychotropic disorder.

13. A method for treating psychotropic disorders which comprises administering an effective amount of the compound of claim 2 to a patient suffering from a psychotropic disorder.

14. A method for treating depression or anxiety which comprises administering a pharmacologically effective amount of the composition of claim 10 to a depressed or anxious patient.

15. A method for treating depression or anxiety which comprises administering a pharmacologically effective amount of the compound of claim 2 to a depressed or anxious patient.

* * * * *